(12) United States Patent
Or et al.

(10) Patent No.: US 7,049,417 B2
(45) Date of Patent: May 23, 2006

(54) 6,11-4-CARBON BRIDGED KETOLIDES

(75) Inventors: Yat Sun Or, Watertown, MA (US); Guoqiang Wang, Belmont, MA (US); Deqiang Niu, Lexington, MA (US); Ly Tam Phan, Malden, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 50 days.

(21) Appl. No.: 10/841,206

(22) Filed: May 7, 2004

(65) Prior Publication Data
US 2004/0266998 A1    Dec. 30, 2004

Related U.S. Application Data

(63) Continuation of application No. 10/205,018, filed on Jul. 25, 2002, now Pat. No. 6,841,664.

(51) Int. Cl.
*C07H 1/00* (2006.01)
(52) U.S. Cl. .................. 536/7.2; 536/7.3; 536/7.4; 536/18.5
(58) Field of Classification Search .............. 536/7.2, 536/7.3, 7.4, 18.5
See application file for complete search history.

(56) References Cited

U.S. PATENT DOCUMENTS

| | | |
|---|---|---|
| 4,990,602 A | 2/1991 | Morimoto et al. |
| 5,403,923 A | 4/1995 | Kashimura et al. |
| 5,444,051 A | 8/1995 | Agouridas et al. |
| 5,527,780 A | 6/1996 | Agouridas et al. |
| 5,631,355 A | 5/1997 | Asaka et al. |
| 5,780,605 A | 7/1998 | Or et al. |
| 5,866,549 A | 2/1999 | Or et al. |
| 5,922,683 A | 7/1999 | Or et al. |
| 5,969,161 A | 10/1999 | Bonnet et al. |
| 6,046,171 A | 4/2000 | Or et al. |
| 6,075,133 A | 6/2000 | Or et al. |
| 6,124,269 A | 9/2000 | Phan et al. |
| 6,274,715 B1 | 8/2001 | Or et al. |
| 6,355,620 B1 | 3/2002 | Ma et al. |
| 6,399,582 B1 | 6/2002 | Hlasta et al. |
| 6,878,691 B1 | 4/2005 | Or et al. |
| 2004/0053861 A1 | 3/2004 | Or et al. |
| 2004/0157787 A1 | 8/2004 | Or et al. |
| 2004/0171818 A1 | 9/2004 | Xu et al. |
| 2005/0009761 A1 | 1/2005 | Or et al. |
| 2005/0009763 A1 | 1/2005 | Or et al. |
| 2005/0014707 A1 | 1/2005 | Wang et al. |
| 2005/0159370 A1 | 7/2005 | Or et al. |
| 2005/0171033 A1 | 8/2005 | Qiu et al. |

FOREIGN PATENT DOCUMENTS

WO    WO 99/21864    5/1999

OTHER PUBLICATIONS

Ma, Zhenkun, et al., "Regioselective Synthesis of Bifunctional Macrolides for Probing Ribosomal Binding," *Organic Letters*, 4(6):987-990 (2002).
U.S. Appl. No. 11/154,260, filed Jun. 16, 2005, Deqiang Niu et al.
U.S. Appl. No. 11/029,640, filed Jan. 5, 2005, Nha Huu Vo et al.
U.S. Appl. No 11/057,476 filed Feb. 14, 2005, Datong Tang et al.
U.S. Appl. No. 11/122,251, filed May 4, 2005, Guoqiang Wang et al.
U.S. Appl. No. 11/257,680, filed Oct. 25, 2005, Wang et al.

*Primary Examiner*—Elli Peselev
(74) *Attorney, Agent, or Firm*—Elmore Patent Law Group, P.C.; Darlene A. Vanstone; Carolyn S. Elmore

(57) ABSTRACT

Novel 6,11-4-carbon bridged ketolides, pharmaceutically-acceptable compositions comprising a therapeutically effective amount of a compound of the invention in combination with a pharmaceutically-acceptable carrier are described. Also described are a method for treating bacterial infections by administering to an animal a pharmaceutical composition containing a therapeutically effective amount of a compound of the invention and processes for the preparation of such compounds.

5 Claims, No Drawings

6,11-4-CARBON BRIDGED KETOLIDES

CROSS-REFERENCE TO RELATED APPLICATIONS

This application is a continuation of U.S. patent application Ser. No. 10/205,018, filed on Jul. 25, 2002, now U.S. Pat. No. 6,841,664. This application is also related to U.S. patent application Ser. No. 10/205,357, filed on Jul. 25, 2002, now U.S. Pat. No. 6,753,318. The entire teachings of the above applications are incorporated herein by reference.

TECHNICAL FIELD

The present invention relates to novel semisynthetic macrolides having antibacterial activity that are useful in the treatment and prevention of bacterial infections. More particularly, the invention relates to 6,11-4-carbon bridged ketolide compounds, compositions containing such compounds and methods for using the same, as well as processes for making such compounds.

BACKGROUND OF THE INVENTION

The spectrum of activity of macrolides, including erythromycin, covers most relevant bacterial species responsible for upper and lower respiratory tract infections. 14-membered ring macrolides are well known for their overall efficacy, safety and lack of serious side effects. Erythromycin however is quickly degraded into inactive products in the acidic medium of the stomach resulting in low bioavailability and gastrointestinal side effects. Improvement of erythromycin pharmacokinetics has been achieved through the synthesis of more acid-stable derivatives, for example, roxithromycin, clarithromycin, and the 15-membered ring macrolide azithromycin. However, all these drugs, including 16-membered ring macrolides, present several drawbacks. They are inactive against $MLS_B$-resistant streptococci ($MLS_B$=Macrolides-Lincosamides-type B Streptogramines) and with the exception of azithromycin, weakly active against *Haemophilus influenzae*. Futhermore, the resistance of *Streptococcus pneumoniae* to erythromycin has increased significantly in recent years (5% to above 40%). There is a high percentage of cross-resistance to penicillin among these isolates, with a worldwide epidemic spread of 10–40% in some areas.

There is, therefore, a clear need for new macrolides that overcome the problem of pneumococcal resistance, have good pharmacokinetic properties and acid stability while continuing to be active against *H. influenzae*. These new macrolides will be ideal candidates for drug development in the first line therapy of upper respiratory tract infections ("URTI") and lower respiratory tract infections ("LRTI").

Macrolides possessing a 3-oxo moiety in place of the 3-cladinose sugar are called "ketolides." These sophisticated molecules have displayed a significant in vitro and in vivo activity against *H. influenzae* and multiresistant pneumococci (Agouridas et al., *J. Med. Chem.* 1998, 41, 4080–4100). It has been postulated that the aryl group tethered to the macrolide skeleton is crucial for activity against $MLS_B$ resistance and the C-3 keto group is important for the improved activity against efflux resistance (Ma, Or et al., *J. Med. Chem.* 2001, 44, 4137–4156).

U.S. Pat. No. 5,444,051 discloses certain 6-O-substituted-3-oxoerythromycin A derivatives. PCT application WO 97/10251, published Mar. 20, 1997, discloses intermediates useful for preparation of 6-O-methyl 3-descladinose erythromycin derivatives. U.S. Pat. No. 5,631,355 discloses certain tricyclic 6-O-methyl 3-oxo erythromycin derivatives. U.S. Pat. No. 5,527,780 discloses certain bicyclic 6-O-methyl-3-oxo erythromycin A derivatives (Agouridas, ROUSSEL) corresponding to EP application 596802, published May 11, 1994. U.S. Pat. Nos. 5,866,549 and 6,075,011, and PCT application WO 00/78773, published Dec. 28, 2000, disclose certain 6-O-substituted erythromycin derivatives. U.S. Pat. No. 6,124,269 and PCT application WO 00/62783, published Oct. 26, 2000, disclose certain 2-halo-6-O-substituted ketolide derivatives. U.S. Pat. No. 6,046,171 and PCT application WO 99/21864, published May 6, 1999, disclose certain 6,11-bridged erythromycin derivatives.

SUMMARY OF THE INVENTION

The present invention provides a novel class of C6–C11 bridged ketolide compounds that possess antibacterial activity.

In one embodiment, the compounds of the present invention are represented by formula I, as illustrated below:

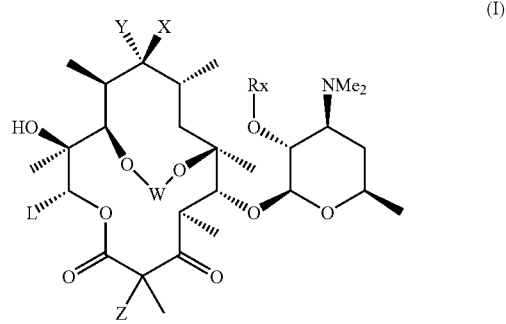

(I)

or the pharmaceutically acceptable salts, esters and prodrugs thereof, wherein
W is selected from the group consisting of:
(a) —$CH_2$—C(A)=C(B)—$CH_2$—;
wherein,
A and B are independently selected from the group consisting of:
(i) hydrogen;
(ii) deuterium;
(iii) halogen;
(iv) $R_1$, wherein $R_1$ is selected from the group consisting of:
  a. $C_1$–$C_6$ alkyl, optionally substituted with one or more substituents selected from the group consisting of: halogen, aryl, substituted aryl, heteroaryl, and substituted heteroaryl;
  b. $C_2$–C6 alkenyl, optionally substituted with one or more substituents selected from the group consisting of: halogen, aryl, substituted aryl, heteroaryl, and substituted heteroaryl; and
  c. $C_2$–$C_6$ alkynyl, optionally substituted with one or more substituents selected from the group consisting of: halogen, aryl, substituted aryl, heteroaryl, and substituted heteroaryl;
(v) $R_2$, wherein $R_2$ is selected from the group consisting of:
  a. aryl;
  b. heteroaryl;

c. substituted aryl; and
d. substituted heteroaryl;
(vi) —($C_1$–$C_3$-alkyl)-M-($C_1$–$C_3$-alkyl)-$R_2$, wherein M=—O—, —NH—, —N($CH_3$)—, —NHC(O)— or —S(O)$_n$—, wherein n=0, 1 or 2, and $R_2$ is as previously defined;
(vii) —($C_1$–$C_3$-alkyl)-M-$R_2$, wherein M and $R_2$ are as previously defined;
(viii) —C(O)-J-$R_3$, wherein J is absent, O or S, and $R_3$ is H, $R_1$ or $R_2$; where $R_1$ and $R_2$ are as previously defined, and
(ix) —C(O)—$NR_{11}R_{12}$, wherein $R_{11}$ and $R_{12}$ are each independently selected from the group consisting of:
a. hydrogen;
b. $C_1$–$C_6$-alkyl, optionally substituted with one or more substituents selected from the group consisting of: halogen, aryl, substituted aryl, heteroaryl, and substituted heteroaryl;
c. $C_2$–$C_6$-alkenyl, optionally substituted with one or more substituents selected from the group consisting of: halogen, aryl, substituted aryl, heteroaryl, and substituted heteroaryl;
d. $C_2$–$C_6$-alkynyl, optionally substituted with one or more substituents selected from the group consisting of: halogen, aryl, substituted aryl, heteroaryl, and substituted heteroaryl; and
e. $R_{11}$ and $R_{12}$ taken together with the nitrogen atom to which they are connected form a 3- to 7-membered ring which may optionally contain one or more heterofunctions selected from the group consisting of: —O—, —NH—, —N($C_1$–$C_6$-alkyl)-, —N($R_2$)—, —S(O)$_n$—, wherein n and $R_2$ are as previously defined;
(b) —$CH_2$—CH(A)-C(B)=CH—, wherein A and B are as previously defined;
(c) —$CH_2$—CH(E)-CH(G)-$CH_2$—;
wherein E and G are independently selected from the group consisting of:
(i) A, wherein A is as previously defined;
(ii) —OH;
(iii) —$OR^p$, wherein $R^p$ is a hydroxy protecting group;
(iv) —O—$R_9$, wherein $R_9$ is $R_1$ or $R_2$, and wherein $R_1$ and $R_2$ are as previously defined;
(v) —S(O)$_n R_9$, wherein n and $R_9$ are as previously defined;
(vi) —NHC(O)$R_3$, wherein $R_3$ is as previously defined;
(vii) —NHC(O)$NR_{11}R_3$, wherein $R_{11}$ and $R_3$ are as previously defined;
(viii) —NHS(O)$_2 R_9$, wherein $R_9$ is as previously defined;
(ix) —$NHR_{13}$, wherein $R_{13}$ is an amino protecting group; and
(x) —$NR_{11}R_{12}$, wherein $R_{11}$ and $R_{12}$ are as previously defined;

(d)

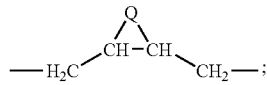

wherein:
(i) -Q- is selected from the group consisting of: —O—; —O—C(O)—CH($R_7$)—; —N($R_7$)—; —O—C(O)—N($R_7$)—; —O—C(O)—O—; —N($R_7$)—N=N—; —C($R_7$)=N—O—and —CH($R_7$)—N($R_8$)—O—; wherein $R_7$ and $R_8$ are independently selected from $R_3$, wherein $R_3$ is as previously defined; or
(ii) -Q- taken together with the two carbon atoms it is attached to is selected from the group consisting of:
a. cycloalkylene;
b. cycloalkenylene; and
c. heterocycloalkylene; and
(e) —$CH_2$—C($R_4$)($R_5$)—$CH_2$—$CH_2$—;
wherein $R_4$ and $R_5$ taken together with the carbon atom to which they are attached are selected from the group consisting of:
(i) C=O;
(ii) C($OR_1$)$_2$, wherein $R_1$ is as previously defined;
(iii) C($SR_1$)$_2$, wherein $R_1$ is as previously defined;
(iv) C[—O($CH_2$)$_m$]$_2$, wherein m is 2 or 3;
(v) C[—S($CH_2$)$_m$]$_2$, wherein m is as previously defined,
(vi) C=$CHR_3$, wherein $R_3$ is as previously defined;
(vii) C=N—O—$R_3$, wherein $R_3$ is as previously defined;
(viii) C=$NNHR_3$, wherein $R_3$ is as previously defined;
(ix) C=NNHC(O)$R_3$, wherein $R_3$ is as previously defined;
(x) C=NNHC(O)$NR_{11}R_3$, wherein $R_{11}$ and $R_3$ are as previously defined;
(xi) C=NNHS(O)$_2 R_9$, wherein $R_9$ is as previously defined;
(xii) C=$NNHR_{13}$, wherein $R_{13}$ is as previously defined; and
(xiii) C=$NR_9$, wherein $R_9$ is as previously defined;
X and Y are:
(a) independently selected from the group consisting of:
(i) hydrogen;
(ii) deuterium;
(iii) —OH;
(iv) —$OR^p$, wherein $R^p$ is as previously defined; and
(v) —$NR_{14}R_{15}$, wherein $R_{14}$ and $R_{15}$ are each independently selected from the group consisting of:
a. hydrogen;
b. $C_1$–$C_{12}$ alkyl, optionally substituted with one or more substituents selected from the group consisting of halogen, aryl, substituted aryl, heteroaryl and substituted heteroaryl; and
c. $R_{14}$ and $R_{15}$, taken together with the nitrogen atom to which they are attached form a 3 to 10 membered heterocycloalkyl ring optionally substituted with one or more hetero atoms selected from the group consisting of O, S and N; or
(b) taken together with the carbon atom to which they are attached are selected from the group consisting of:
(i) C=O;
(ii) C=$NR_3$, wherein $R_3$ is as previously defined;
(iii) C=NC(O)$R_3$, wherein $R_3$ is as previously defined;
(iv) C=N—$OR_6$, wherein $R_6$ is selected from the group consisting of:
a. hydrogen;
b. —$CH_2$O($CH_2$)$_2$$OCH_3$;
c. —$CH_2$O($CH_2$O)$_n$$CH_3$, wherein n is as previously defined;

d. $C_1-C_{12}$ alkyl, optionally substituted with one or more substituents selected from the group consisting of halogen, aryl, substituted aryl, heteroaryl and substituted heteroaryl;

e. $C_3-C_{12}$ cycloalkyl;

f. $C(O)-C_1-C_{12}$ alkyl;

g. $C(O)-(C_3-C_{12}$ cycloalkyl);

h. $C(O)-R_2$, wherein $R_2$ is as previously defined; and i. $-Si(R_a)(R_b)(R_c)$, wherein $R_a$, $R_b$ and $R_c$ are each independently selected from the group consisting of $C_1-C_{12}$ alkyl, aryl and substituted aryl;

(v) $C=N-O-C(R_{16})(R_{17})-O-R_{18}$, wherein $R_{16}$ and $R_{17}$ taken together with the carbon atom to which they are attached form a $C_3$ to $C_{12}$ cycloalkyl group or each independently is selected from the group consisting of: hydrogen and $C_1-C_{12}$ alkyl; and $R_{18}$ is selected from the group consisting of:

a. hydrogen;

b. $-CH_2O(CH_2)_2OCH_3$;

c. $-CH_2O(CH_2O)_nCH_3$, wherein n is as previously defined;

d. $C_1-C_{12}$ alkyl, optionally substituted with one or more substituents selected from the group consisting of halogen, aryl, substituted aryl, heteroaryl and substituted heteroaryl;

e. $C_3-C_{12}$ cycloalkyl; and f. $-Si(R_a)(R_b)(R_c)$, wherein $R_a$, $R_b$ and $R_c$ are as previously defined;

L is selected from the group consisting of:

(a) $-CH(OH)CH_3$;

(b) $C_1-C_6$ alkyl, optionally substituted with one or more substituents selected from the group consisting of aryl, substituted aryl, heteroaryl, and substituted heteroaryl;

(c) $C_2-C_6$ alkenyl, optionally substituted with one or more substituents selected from the group consisting of aryl, substituted aryl, heteroaryl, and substituted heteroaryl; and (d) $C_2-C_6$ alkynyl, optionally substituted with one or more substituents selected from the group consisting of aryl, substituted aryl, heteroaryl, and substituted heteroaryl;

Z is selected from the group consisting of:

(a) hydrogen;

(b) methyl; and (c) halogen; and $R_x$ is hydrogen or $R^p$, wherein $R^p$ is as previously defined.

In another aspect of the present invention, pharmaceutical compositions are disclosed that comprise a therapeutically effective amount of a compound of the invention in combination with a pharmaceutically acceptable carrier. The invention also includes a method of treatment of antibacterial infections with such compositions. Suitable carriers and methods of formulation are also disclosed. The compounds and compositions of the present invention have antibacterial activity.

In a further aspect of the present invention, processes for the preparation of 6,11-4 carbon bridged ketolides of formula I are provided.

DETAILED DESCRIPTION OF THE INVENTION

In a first embodiment of the compounds of the present invention are compounds represented by formula I as illustrated above, or a pharmaceutically acceptable salt, ester or prodrug thereof.

In a second embodiment of the compounds of the present invention are compounds represented by formula II as illustrated below, or a pharmaceutically acceptable salt, ester or prodrug thereof:

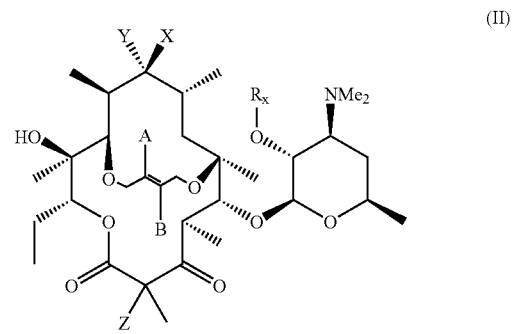

(II)

where A, B, X, Y, Z and $R_x$ are as previously defined.

In a third embodiment of the compounds of the present invention are compounds represented by formulae III a or III b as illustrated below, or a pharmaceutically acceptable salt, ester or prodrug thereof:

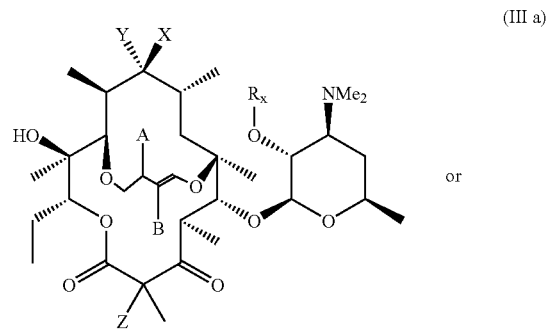

(III a)

or

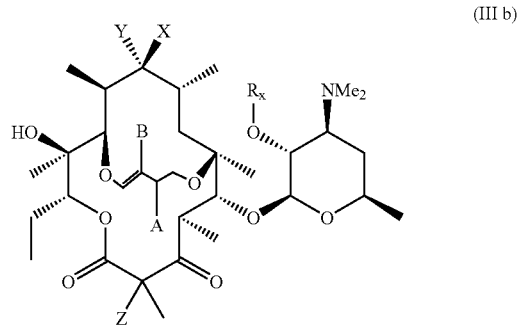

(III b)

where A, B, X, Y, Z and $R_x$ are as previously defined.

In a fourth embodiment of the compounds of the present invention are compounds represented by formula IV as illustrated below, or a pharmaceutically acceptable salt, ester or prodrug thereof:

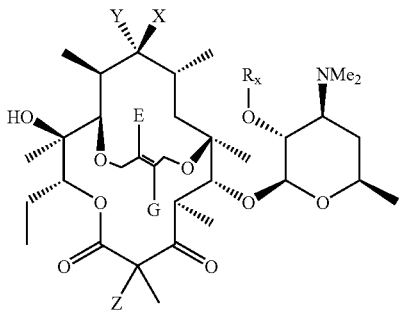
(IV)

where E, G, X, Y, Z and $R_x$ are as previously defined.

In a fifth embodiment of the compounds of the present invention are compounds represented by formula V as illustrated below, or a pharmaceutically acceptable salt, ester or prodrug thereof:

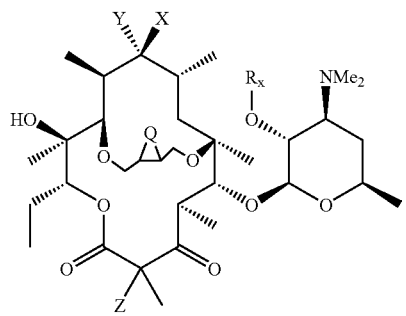
(V)

where Q, X, Y, Z and $R_x$ are as previously defined.

In a sixth embodiment of the compounds of the present invention are compounds represented by formulae VI a or VI b as illustrated below, or a pharmaceutically acceptable salt, ester or prodrug thereof:

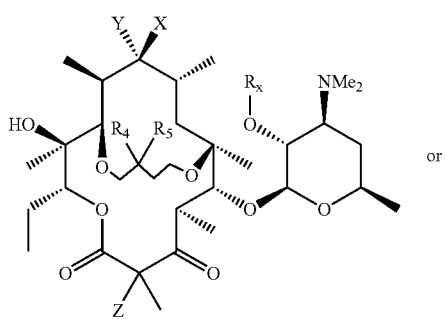
(VI a)

or

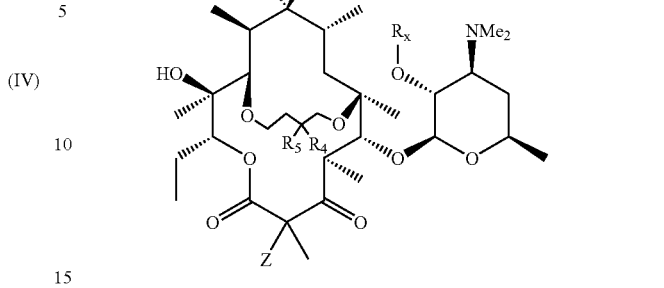
(VI b)

where X, Y, Z, $R_x$, $R_4$ and $R_5$ are as previously defined.

Another preferred embodiment of the present invention comprises compounds represented by any of the above formulas I through VI wherein: X and Y taken together with the carbon atom they are attached to are selected from the group consisting of: C=O, C=NR$_3$, C=N—O—R$_6$, C=N—C(O)R$_3$ and C=N—O—C(R$_{16}$)(R$_{17}$)—O—R$_{18}$; Z is hydrogen and $R_x$ is hydrogen, where $R_3$, $R_6$, $R_{16}$, $R_{17}$ and $R_{18}$ are as previously defined.

Yet another preferred embodiment of the invention comprises compounds represented by formula I wherein L is $CH_2CH_3$.

Representative compounds according to the invention are those selected from the group consisting of:

Compound of Formula (I): W=—CH$_2$CH=CHCH$_2$—; X and Y taken together with the carbon atom they are attached to =C=NC(O)CH$_3$; L=CH$_2$CH$_3$; Z=H and R$_x$=H;

Compound of Formula (I): W=—CH$_2$CH=CHCH$_2$—; X and Y taken together with the carbon atom they are attached to =C=NH; L=CH$_2$CH$_3$; Z=H and R$_x$=H;

Compound of Formula (I): W=—CH$_2$CH=CHCH$_2$—; X and Y taken together with the carbon atom they are attached to =C=N—OCH$_2$OCH$_3$; L=CH$_2$CH$_3$; Z=H and R$_x$=H;

Compound of Formula (I): W=—CH$_2$CH=CHCH$_2$—; X and Y taken together with the carbon atom they are attached to =C=N—OH; L=CH$_2$CH$_3$; Z=H and R$_x$=C(O)C$_6$H$_5$;

Compound of Formula (I): W=—CH$_2$CH=CHCH$_2$—; X and Y taken together with the carbon atom they are attached to =C=N—O—CH$_2$—OCH$_3$; L=CH$_2$CH$_3$; Z=H and R$_x$=C(O)C$_6$H$_5$;

Compound of Formula (I): W=—CH$_2$CH=CHCH$_2$—; X and Y taken together with the carbon atom they are attached to =C=O; L=CH$_2$CH$_3$; Z=H and R$_x$=C(O)CH$_3$;

Compound of Formula (I): W=—CH$_2$CH=CHCH$_2$—; X and Y taken together with the carbon atom they are attached to =C=O; L=CH$_2$CH$_3$; Z=H and R$_x$=H;

Compound of Formula (I): W=—CH$_2$—CH(3-quinolyl)-CH=CH—; X and Y taken together with the carbon atom they are attached to =C=NC(O)CH$_3$; L=CH$_2$CH$_3$; Z=H and R$_x$=H;

Compound of Formula (III a): A=3-quinolyl; B=H; X and Y taken together with the carbon atom they are attached to =C=NC(O)CH$_3$; Z=H and R$_x$=H;

Compound of Formula (V): Q=—C($C_6H_5$)=N—O—; X and Y taken together with the carbon atom they are attached to =C=NC(O)$CH_3$; Z=H and $R_x$=H;

Compound of Formula (V): Q=—O—C(O)—O—; X and Y taken together with the carbon atom they are attached to =C=NC(O)$CH_3$; Z=H and $R_x$=H;

Compound of Formula (I): W=—$CH_2$CH=CH$CH_2$—; X and Y taken together with the carbon atom they are attached to =C=N—C(O)$CH_2$O$CH_3$; L=$CH_2$$CH_3$; Z=H and $R_x$=H;

Compound of Formula (V): Q=—O—; X and Y taken together with the carbon atom they are attached to =C=NC(O)$CH_3$; Z=H and $R_x$=H; and Compound of Formula (I): W=—$CH_2$—C(CH=CH—$C_6H_5$)=CH—$CH_2$—; X and Y taken together with the carbon atom they are attached to =C=NC(O)$CH_3$; L=$CH_2$$CH_3$; Z=H and $R_x$=H.

Definitions

The terms "$C_1$–$C_3$ alkyl," "$C_1$–$C_6$ alkyl" or "$C_1$–$C_{12}$ alkyl," as used herein, refer to saturated, straight- or branched-chain hydrocarbon radicals containing between one and three, one and twelve, or one and six carbon atoms, respectively. Examples of $C_1$–$C_3$ alkyl radicals include methyl, ethyl, propyl and isopropyl radicals; examples of $C_1$–$C_6$ alkyl radicals include, but are not limited to, methyl, ethyl, propyl, isopropyl, n-butyl, tert-butyl, neopentyl and n-hexyl radicals; and examples of $C_1$–$C_{12}$ alkyl radicals include, but are not limited to, ethyl, propyl, isopropyl, n-hexyl, octyl, decyl, dodecyl radicals.

The term "substituted alkyl" or "alkyl substituent" refers to an alkyl group substituted by, for example, one to four substituents, such as, halo, phenyl, substituted phenyl, heterocyclo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkysulfonyl, arylsulfonyl, aralkylsulfonyl, sulfonamido (e.g. $SO_2NH_2$), substituted sulfonamido, nitro, cyano, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidine and heterocyclos, such as, indolyl, imidazolyl, furyl, thienyl, thiazolyl, pyrrolidyl, pyridyl, pyrimidyl, and the like. Where, if noted above, the substituent is further substituted, it will be with halogen, alkyl, alkoxy, aryl or aralkyl.

The term "aralkyl" refers to an aryl group bonded directly through an alkyl group, such as benzyl.

The term "alkylene" denotes a divalent group derived from a straight or branched chain saturated hydrocarbon by the removal of two hydrogen atoms, for example, methylene, 1,2-ethylene, 1,1-ethylene, 1,3-propylene, and the like.

The terms "$C_2$–$C_{12}$ alkenyl" or "$C_2$–$C_6$ alkenyl," as used herein, denote a monovalent group derived from a hydrocarbon moiety containing from two to twelve or two to six carbon atoms having at least one carbon-carbon double bond by the removal of a single hydrogen atom. Alkenyl groups include, but are not limited to, for example, ethenyl, propenyl, butenyl, 1-methyl-2-buten-1-yl, and the like.

The term "alkenylene" denotes a divalent group derived from an alkenyl group as defined previously by the removal a second hydrogen atom, containing from two to twelve carbon atoms and having at least one carbon-carbon double bond, for example, 1,2-ethenyl, 1,2-propylene, 1,4-butenyl, 1-methyl-but-1-en-1,4-yl, and the like.

The terms "$C_2$–$C_{12}$ alkynyl" or "$C_2$–$C_6$ alkynyl," as used herein, denote a monovalent group derived from a hydrocarbon moiety containing from two to twelve or two to six carbon atoms having at least one carbon-carbon triple bond by the removal of two hydrogen atoms. Representative alkynyl groups include, but are not limited to, for example, ethynyl, 1-propynyl, 1-butynyl, and the like.

The terms "halo" and "halogen," as used herein, refer to an atom selected from fluorine, chlorine, bromine and iodine.

The term "haloalkyl" denotes an alkyl group, as defined above, having one, two or three halogen atoms attached thereto and is exemplified by such groups as chloromethyl, bromoethyl, trifluoromethyl, and the like.

The term "aryl," as used herein, refers to a mono- or bicyclic carbocyclic ring system having one or two aromatic rings including, but not limited to, phenyl, naphthyl, tetrahydronaphthyl, indanyl, idenyl and the like. Aryl groups (including bicyclic aryl groups) can be unsubstituted or substituted with one, two or three substitutents independently selected from loweralkyl, substituted loweralkyl, haloalkyl, alkoxy, thioalkoxy, amino, alkylamino, dialkylamino, acylamino, cyano, hydroxy, halo, mercapto, nitro, carboxaldehyde, carboxy, alkoxycarbonyl and carboxamide. In addition, substituted aryl groups include tetrafluorophenyl and pentafluorophenyl.

The term "arylene" denotes a divalent group derived from an aryl moiety as defined previously by the removal of a second hydrogen atom. Arylene groups include, for example, 1,2-phenyl, 1,3-phenyl, 1,4-phenyl, 1,2-naphthyl, 1,4-naphthyl, 1,6-naphthyl, and the like.

The term "substituted aryl," as used herein, refers to an aryl group, as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)—$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_2CF_3$, $CHCl_2$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkylamino, thio, aryl-thio, heteroarylthio, benzyl-thio, $C_1$–$C_6$-alkyl-thio, or methylthiomethyl.

The term "substituted arylene" as used herein refers to an arylene group as defined herein substituted by independent replacement of one, two or three of the hydrogen atoms thereon with halo, hydroxyl, cyano, $C_1$–$C_3$-alkyl, $C_1$–$C_6$-alkoxy, $C_1$–$C_6$-alkoxy substituted with aryl, haloalkyl, thioalkoxy, amino, alkylamino, dialkylamino, acylamino, mercapto, nitro, carboxaldehyde, carboxyl, alkoxycarbonyl and carboxamide. In addition, any one substituent may be an aryl, heteroaryl, or heterocycloalkyl group. Also, substituted aryl groups include tetrafluorophenyl and pentafluorophenyl.

The term "heteroaryl," as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

The term "heteroarylene" denotes a divalent group derived from a heteroaryl moiety as defined previously by the removal a second hydrogen atom. Heteroarylene groups include, for example, 2,3-pyridyl, 2,4-pyridyl, 2,6-pyridyl, 2,3-quinolyl, 2,4-quinolyl, 2,6-quinolyl, 1,4-isoquinolyl, 1,6-isoquinolyl, and the like.

The term "substituted heteroaryl," as used herein, refers to a heteroaryl group as defined herein, substituted by independent replacement of one, two or three of the hydrogen atoms thereon with F, Cl, Br, I, OH, $NO_2$, CN, C(O)—$C_1$–$C_6$-alkyl, C(O)-aryl, C(O)-heteroaryl, $CO_2$-alkyl, $CO_2$-aryl, $CO_2$-heteroaryl, $CONH_2$, CONH—$C_1$–$C_6$-alkyl, CONH-aryl, CONH-heteroaryl, OC(O)—$C_1$–$C_6$-alkyl, OC(O)-aryl, OC(O)-heteroaryl, $OCO_2$-alkyl, $OCO_2$-aryl, $OCO_2$-heteroaryl, $OCONH_2$, OCONH—$C_1$–$C_6$-alkyl, OCONH-aryl, OCONH-heteroaryl, NHC(O)-$C_1$–$C_6$-alkyl, NHC(O)-aryl, NHC(O)-heteroaryl, $NHCO_2$-alkyl, $NHCO_2$-aryl, $NHCO_2$-heteroaryl, $NHCONH_2$, NHCONH—$C_1$–$C_6$-alkyl, NHCONH-aryl, NHCONH-heteroaryl, $SO_2$—$C_1$–$C_6$-alkyl, $SO_2$-aryl, $SO_2$-heteroaryl, $SO_2NH_2$, $SO_2NH$—$C_1$–$C_6$-alkyl, $SO_2NH$-aryl, $SO_2NH$-heteroaryl, $C_1$–$C_6$-alkyl, $C_3$–$C_6$-cycloalkyl, $CF_3$, $CH_{CHCl2}$, $CH_2OH$, $CH_2CH_2OH$, $CH_2NH_2$, $CH_2SO_2CH_3$, aryl, heteroaryl, benzyl, benzyloxy, aryloxy, heteroaryloxy, $C_1$–$C_6$-alkoxy, methoxymethoxy, methoxyethoxy, amino, benzylamino, arylamino, heteroarylamino, $C_1$–$C_3$-alkyl-amino, thio, aryl-thio, heteroarylthio, benzyl-thio, $C_1$–$C_6$-alkyl-thio, or methylthiomethyl.

The term "substituted heteroarylene," as used herein, refers to a heteroarylene group as defined herein substituted by independent replacement of one, two or three, of the hydrogen atoms thereon with Cl, Br, F, I, OH, CN, C1–C3-alkyl, C1–C6-alkoxy, C1–C6-alkoxy substituted with aryl, haloalkyl, thioalkoxy, amino, alkylamino, dialkylamino, mercapto, nitro, carboxaldehyde, carboxy, alkoxycarbonyl, and the like. In addition, any one substituent may be an aryl, heteroaryl, or heterocycloalkyl group.

The term "$C_3$–$C_{12}$-cycloalkyl" or "cycloalkyl," as used herein, refers to a monovalent group derived from a monocyclic or bicyclic saturated carbocyclic ring compound by the removal of a single hydrogen atom. Examples include, but are not limited to, cyclopropyl, cyclobutyl, cyclopentyl, cyclohexyl, bicyclo [2.2.1] heptyl, and bicyclo [2.2.2] octyl.

The term "heterocycloalkyl," as used herein, refers to a non-aromatic 3- to 7-membered ring or a bi- or tri-cyclic group comprising fused six-membered rings having between one and three heteroatoms independently selected from oxygen, sulfur and nitrogen, wherein (i) each 5-membered ring has 0 to 1 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl.

The term "cycloalkylene" refers to a divalent cycloalkyl moiety with two hydrogen atoms removed—one each from two adjacent carbon atoms—derived by the removal of the two hydrogen atoms from a cycloalkyl group as previously defined that is optionally substituted, or from saturated cyclic hydrocarbon ring systems, preferably containing 1 to 3 rings and 3 to 7 carbons per ring which may be further fused to an unsaturated C3–C7 carbocyclic ring. Exemplary cycloalkyl groups from which the cycloalkylene groups can be derived include cyclopropyl, cyclobutyl, cyclopentyl, cyclohexyl, cycloheptyl, cyclooctyl, cyclodecyl, cyclododecyl, and adamantly. Exemplary substituents include one or more alkyl, aryl, heteroaryl groups as described above, or one or more groups described above as alkyl substituents.

The term "cycloalkenylene" refers to a divalent cycloalkenyl moiety with two hydrogen atoms removed—one each from two adjacent carbon atoms—derived by the removal of the two hydrogen atoms from a cycloalkenyl group that contains one or more unsaturated double bonds optionally substituted, or from unsaturated cyclic ring systems, preferably containing 1 to 3 rings and 3 to 7 carbons per ring which may be further fused with an unsaturated C3–C7 carbocyclic ring. Exemplary cycloalkenyl groups from which the cycloalkenylene groups can be derived include cyclopropenyl, cyclobutenyl, cyclopentenyl, cyclohexenyl, and the like. Exemplary substituents include one or more alkyl, aryl, heteroaryl groups as described above, or one or more groups described above as alkyl substituents.

The term "heterocycloalkylene" refers to a divalent heterocyclic moiety with two hydrogen atoms removed—one each from two adjacent carbon atoms—derived by the removal of the two hydrogen atoms from a heterocycloalkyl group previously defined that is optionally substituted, or from a fully saturated or unsaturated, nonaromatic cyclic group which may be further fused with or substituted with an aromatic ring, for example, which is a 3 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom. Exemplary monocyclic heterocyclic groups from which the heterocycloalkylene groups can be derived include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolidinyl, isoxazolyl, thiazolyl, thiadiazolyl, thiazolidinyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1,1-dioxothienyl, dioxanyl, isothiazolidinyl, thietanyl, thiiranyl, triazinyl, and triazolyl, and the like. Exemplary bicyclic heterocyclic groups from which the heterocycloalkylene groups can be derived include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl or furo[2,3-b]pyridinyl), dihydroisoindolyl, dihydroquinazolinyl, (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like. Exemplary substituents include one or more alkyl, aryl or heteroaryl groups as described above or one or more groups described above as alkyl substituents. Also included are smaller heterocyclics, such as epoxides and aziridines.

The term "heteroatoms" includes, but is not limited to, oxygen, sulfur and nitrogen.

The term "$C_1$–$C_6$ alkoxy," as used herein, refers to a $C_1$–$C_6$ alkyl group, as previously defined, attached to the parent molecular moiety through an oxygen atom. Examples of $C_1$–$C_6$-alkoxy include, but are not limited to, methoxy, ethoxy, propoxy, isopropoxy, n-butoxy, tert-butoxy, neopentoxy and n-hexoxy.

The term "$C_1$–$C_3$-alkyl-amino," as used herein, refers to one or two $C_1$–$C_3$-alkyl groups, as previously defined, attached to the parent molecular moiety through a nitrogen atom. Examples of $C_1$–$C_3$-alkyl-amino include, but are not limited to methylamino, dimethylamino, ethylamino, diethylamino, and propylamino.

The term "alkylamino" refers to a group having the structure —NH ($C_1$–$C_{12}$ alkyl) where $C_1$–$C_{12}$ alkyl is as previously defined.

The term "dialkylamino" refers to a group having the structure —N ($C_1$–$C_{12}$ alkyl) ($C_1$–$C_{12}$ alkyl), where $C_1$–$C_{12}$ alkyl is as previously defined. Examples of dialkylaminoinclude, but are not limited to, dimethylamino, diethylamino, methylethylamino, piperidino, and the like.

The term "alkoxycarbonyl" represents an ester group, i.e. an alkoxy group, attached to the parent molecular moiety through a carbonyl group such as methoxycarbonyl, ethoxycarbonyl, and the like.

The term "carboxaldehyde," as used herein, refers to a group of formula —CHO.

The term "carboxy," as used herein, refers to a group of formula —COOH.

The term "carboxamide," as used herein, refers to a group of formula —C(O)NH($C_1$–$C_{12}$ alkyl) or —C(O)N($C_1$–$C_{12}$ alkyl) ($C_1$–$C_{12}$ alkyl).

"Hydroxy protecting group," as used herein, refers to an easily removable group such as is known in the art to protect a hydroxy group against undesirable reaction during synthetic procedures and to be selectively removable. The use of hydroxy-protecting groups is well known in the art for protecting groups against undesirable reactions during a synthetic procedure and many such protecting groups are known, cf, for example, T. H. Greene and P. G. M. Wuts, *Protective Groups in Organic Synthesis*,. 3rd edition, John Wiley & Sons, New York (1999). Examples of hydroxy protecting groups include, but are not limited to, methylthiomethyl, tert-dimethylsilyl, tert-butyldiphenylsilyl, acyl substituted with an aromatic group and the like.

The term "protected hydroxy" refers to a hydroxy group protected with a hydroxy protecting group, as defined above, including benzoyl, acetyl, trimethylsilyl, triethylsilyl, methoxymethyl groups, for example.

"Amino protecting group," as used herein, refers to an easily removable group such as is known in the art to protect an amino group against undesirable reaction during synthetic procedures and to be selectively removable. The use of amino-protecting groups is well known in the art for protecting groups against undesirable reactions during a synthetic procedure and many such protecting groups are known, cf, for example, T. H. Greene and P. G. M. Wuts, *Protective Groups in Organic Synthesis*, 3rd edition, John Wiley & Sons, New York (1999). Examples of amino protecting groups include, but are not limited to, 9-fluorenylmethyl carbamate, benzylcarbonate, tert-butylcarbonate, benzyl, p-toluene sulfonyl, acyl and the like.

The term "aprotic solvent," as used herein, refers to a solvent that is relatively inert to proton activity, i.e., not acting as a proton-donor. Examples include, but are not limited to, hydrocarbons, such as hexane and toluene, for example, halogenated hydrocarbons, such as, for example, methylene chloride, ethylene chloride, chloroform, and the like, heterocyclic compounds, such as, for example, tetrahydrofuran and N-methylpyrrolidinone, and ethers such as diethyl ether, bis-methoxymethyl ether. Such compounds are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of aprotic solvents may be found in organic chemistry textbooks or in specialized monographs, for example: *Organic Solvents Physical Properties and Methods of Purification*, 4th ed., edited by John A. Riddick et al, Vol. II, in the Techniques of Chemistry Series, John Wiley & Sons, NY, 1986.

The term "protic solvent" or "protogenic organic solvent," as used herein, refers to a solvent that tends to provide protons, such as an alcohol, for example, methanol, ethanol, propanol, isopropanol, butanol, t-butanol, and the like. Such solvents are well known to those skilled in the art, and it will be obvious to those skilled in the art that individual solvents or mixtures thereof may be preferred for specific compounds and reaction conditions, depending upon such factors as the solubility of reagents, reactivity of reagents and preferred temperature ranges, for example. Further discussions of protogenic solvents may be found in organic chemistry textbooks or in specialized monographs, for example: *Organic Solvents Physical Properties and Methods of Purification*, 4th ed., edited by John A. Riddick et al, Vol. II, in the Techniques of Chemistry Series, John Wiley & Sons, NY, 1986.

Numerous asymmetric centers may exist in the compounds of the present invention. Except where otherwise noted, the present invention contemplates the various stereoisomers and mixtures thereof. Accordingly, whenever a bond is represented by a wavy line, it is intended that a mixture of stereo-orientations or an individual isomer of assigned or unassigned orientation may be present.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters include, but are not limited to, formates, acetates, propionates, butyrates, acrylates and ethylsuccinates.

In addition, zwitterions ("inner salts") may be formed from the compounds of the present invention.

The term "pharmaceutically acceptable prodrugs" as used herein refers to those prodrugs of the compounds of the present invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of the present invention. The term "prodrug" refers to compounds that are rapidly transformed in vivo to yield the parent compound of the above formula, for example by hydrolysis in blood. A thorough discussions is provided in T. Higuchi and V. Stella, "Pro-drugs as Novel Delivery Systems", Vol. 14 of the ACS Symposium Series, and in Edward B. Roche, ed., "Bioreversible Carriers in Drug Design", American Pharmaceutical Association and Pergamon Press, 1987, both of which are incorporated herein by reference.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991);

c) H. Bundgaard, et al., *Advanced Drug Delivery Reviews*, 8, 1–38 (1992);

d) H. Bundgaard, et al., *Journal of Pharmaceutical Sciences*, 77, 285 (1998); and e) N. Kakeya, et al., *Chem Phar Bull*, 32, 692 (1984).

It should further be understood that solvates (e.g., hydrates) of the compounds of the present invention are also within the scope of the present invention. Methods of solvation are generally known in the art.

Antibacterial Activity

Susceptibility tests can be used to quantitatively measure the in vitro activity of an antimicrobial agent against a given bacterial isolate. Compounds were tested for in vitro antibacterial activity by a micro-dilution method. Minimal Inhibitory Concentration (MIC) was determined in 96 well microtiter plates utilizing the appropriate Mueller Hinton Broth medium (CAMHB) for the observed bacterial isolates. Antimicrobial agents were serially diluted (2-fold) in DMSO to produce a concentration range from about 64 $\mu$g/ml to about 0.03 $\mu$g/ml. The diluted compounds (2 $\mu$l/well) were then transferred into sterile, uninoculated CAMHB (0.2 mL) by use of a 96 fixed tip-pipetting station. The inoculum for each bacterial strain was standardized to $5\times10^5$ CFU/mL by optical comparison to a 0.5 McFarland turbidity standard. The plates were inoculated with 10 $\mu$l/well of adjusted bacterial inoculum. The 96 well plates were covered and incubated at 35+/−2° C. for 24 hours in ambient air environment. Following incubation, plate wells were visually examined by Optical Density measurement for the presence of growth (turbidity). The lowest concentration of an antimicrobial agent at which no visible growth occurs was defined as the MIC. The compounds of the invention generally demonstrated an MIC in the range from about 64 $\mu$g/ml to about 0.03 $\mu$g/ml.

All in vitro testing follows the guidelines described in the Approved Standards M7-A4 protocol, published by the National Committee for Clinical Laboratory Standards (NCCLS).

Pharmaceutical Compositions

The pharmaceutical compositions of the present invention comprise a therapeutically effective amount of a compound of the present invention formulated together with one or more pharmaceutically acceptable carriers. As used herein, the term "pharmaceutically acceptable carrier" means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminun hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate. Coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), buccally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such as magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, bacterial infections are treated or prevented in a patient such as a human or other animals by administering to the patient a therapeutically effective amount of a compound of the invention, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment of from about 10 mg to about 1000 mg of the compound(s) of this invention per day in single or multiple doses.

The pharmaceutical compositions of this invention can be administered to fish by blending them in the fish feed to be administered orally or may be dissolved in water in which sick fish are placed to swim around (a method using a so-called "medicated bath"). The dosage for the treatment of fish differs depending upon the purpose of administration (prevention or cure of disease) and type, size and extent of infection of the fish to be treated. Generally, a dosage of 5–1000 mg, preferably 20–1000 mg, per kg of body weight of fish may be administered per day, either at one time or divided into several times. It will be recognized that the above-specified dosage is only a general range which may be reduced or increased depending upon the age, body weight, condition of disease, etc. of the fish.

Abbreviations

Abbreviations which have been used in the description of the schemes and the examples are as follows: AIBN for azobisisobutyronitrile; Boc for tert-Butoxycarbonyl; BSA for bis(trimethylsilyl)acetamide; Bu$_3$SnH for tributyltin hydride; CDI for carbonyldiimidazole; dba for dibenzylideneacetone; DBU for 1,8-diazabicyclo[5.4.0]undec-7-ene; DMAP for 4-N,N-dimethylamino-pyridine; DCC for 1,3-dicyclohexylcarbodiimide; DEAD for diethylazodicarboxylate; DMF for dimethyl formamide; DMSO for dimethylsulfoxide; DPPA for diphenylphosphoryl azide; dppb for 1,4-bis(diphenylphosphino)butane; dppe for 1,2-bis(diphenylphosphino)ethane; EDC for 1-ethyl-3-(3-dimethylaminopropyl)carbodiimide; EtOAc for ethyl acetate; HMDS for 1,1,1,3,3,3-Hexamethyldisilazane; KHMDS for potassium bis(trimethylsilyl)amide; m-CPBA for meta-chloroperbenzoic acid; MeOH for methanol; MOMCl for methoxymethylchloride; NaHMDS for sodium bis(trimethylsilyl)amide; NaN(TMS)$_2$ for sodium bis(trimethylsilyl)amide; NCS for N-Chlorosuccinimide; NMO for N-methylmorpholine N-oxide; PCC for pyridinium chlorochromate; PDC for pyridinium dichromate; Ph for phenyl; TBS for tert-butyl dimethyl silyl; TEA for triethylamine; THF for tetrahydrofuran; TPP for triphenylphosphine; TBAF for tetra-n-butyl ammonium fluoride; TFA for trifluoroacetic acid; TMS for trimethyl silyl; TPAP for tetrapropylammonium perruthenate; Ac for acetyl and Bz for benzoyl.

Synthetic Methods

The compounds and processes of the present invention will be better understood in connection with the following synthetic schemes (schemes 1–11) that are illustrative of the methods to prepare the compounds of the invention and the intermediates useful in their preparation. The groups A, B, $R_3$, $R_6$, $R_9$, $R^p$, X and Y are as defined previously herein unless otherwise noted below. As used in the schemes and examples, the group "V" taken together with the carbon atom it is attached to is selected from the group: C=O, C=NR$_3$, C=N—O—R$_6$, C=N—C(O)R$_3$ and C=N—O—C(R$_{16}$)(R$_{17}$)—O—R$_{18}$; where R$_3$, R$_6$, R$_{16}$, R$_{17}$ and R$_{18}$ are as previously defined. The C-9 position (X, Y) can be further derivatized with suitable procedures that are well-known in the art and those mentioned in PCT publications: WO 00/62783 and WO 98/38199 as well as publications: "Synthetic Modifications of the Erythromycin A Macrolactone: Effects on Biological Activity," Lartey, P. A. and Perun, T. J., Atta-ur-Rahman (Ed.) *Studies in Natural Products Chemistry, Vol.* 13, 1993, and "Recent developments in 14- and 15-membered macrolides," Chu, Daniel T. W., Section Review: Anti-infectives, *Exp. Opin. Invest. Drugs* 1995, 4(2), page 65–94, which are herein incorporated by reference in their entirety.

A preferred intermediate for the preparation of compounds represented by formula I is a compound represented by formula VII as illustrated below:

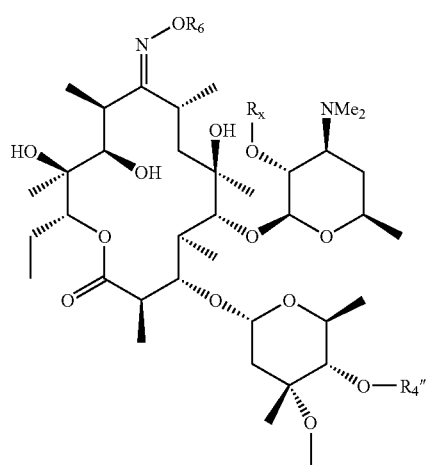

wherein $R_6$ and $R_x$ are as previously defined and $R_4''$ is a hydroxy protecting group.

A second preferred intermediate for the preparation of compounds represented by formula VIII is a compound represented by formula VIII as illustrated below:

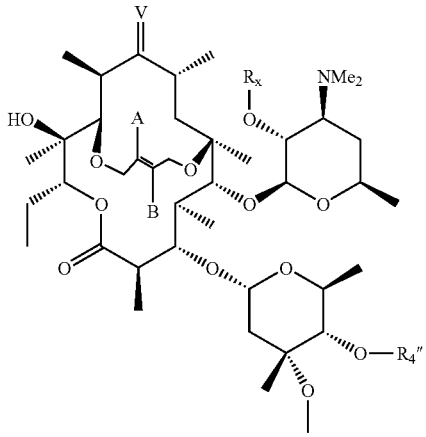

wherein A, B, $R_x$ and $R_4''$ are as previously defined and V taken together with the carbon atom it is attached to is selected from the group: C=O, C=NR$_3$, C=N—O—R$_6$, C=N—C(O)R$_3$ and C=N—O—C(R$_{16}$)(R$_{17}$)—O—R$_{18}$; where $R_3$, $R_6$, $R_{16}$, $R_{17}$ and $R_{18}$ are as previously defined.

A third preferred intermediate for the preparation of compounds represented by formula I is a compound represented by formula IX as illustrated below:

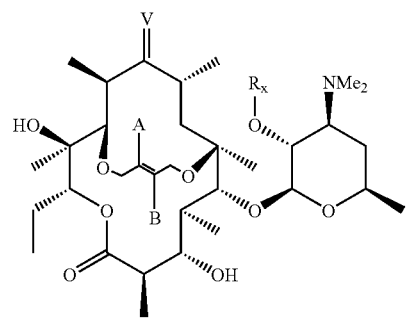

wherein A, B, $R_x$ and V are as previously defined.

A fourth preferred intermediate for the preparation of compounds represented by formula I is a compound represented by formula X as illustrated below:

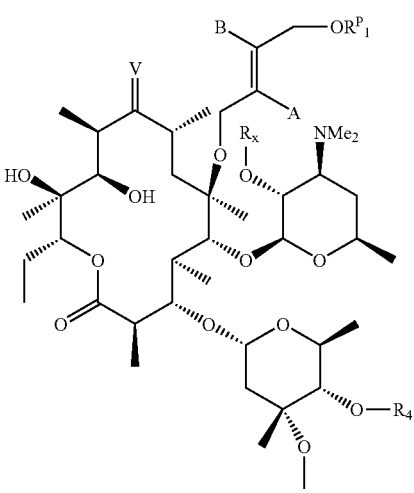

wherein A, B, X, Y, $R_x$, and $R_4''$ are as previously defined and $R^P_1$ is H or $R^P$, where $R^P$ is as previously defined.

A fifth preferred intermediate for the preparation of compounds represented by formula I is a compound represented by formula XI as illustrated below:

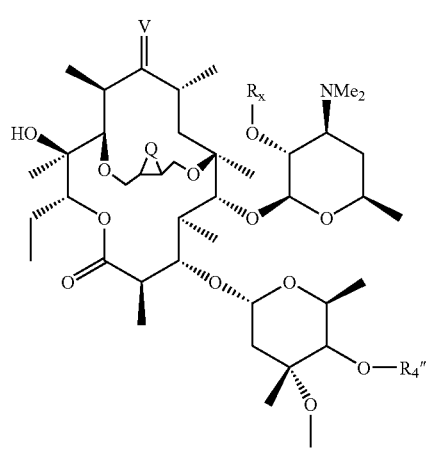

(XI)

wherein Q, $R_x$, $R_4''$ and V are as previously defined.

A sixth preferred intermediate for the preparation of compounds represented by formula I is a compound represented by formula XII as illustrated below:

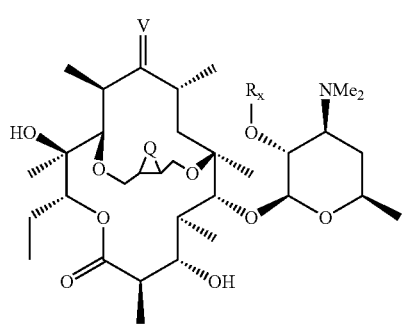

(XII)

wherein Q, $R_x$ and V are as previously defined.

A seventh preferred intermediate for the preparation of compounds represented by formula I is a compound represented by formula XIII as illustrated below:

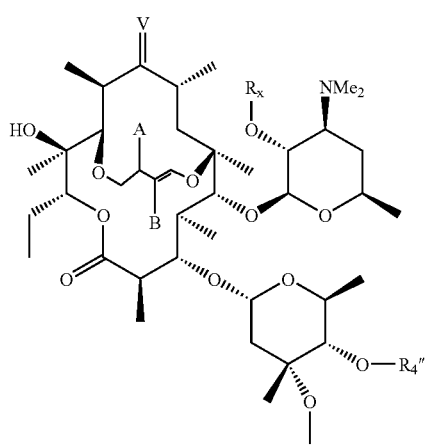

(XIII)

wherein A, B, $R_x$, $R_4''$ and V are as previously defined.

An eighth preferred intermediate for the preparation of compounds represented by formula I is a compound represented by formula XIV as illustrated below:

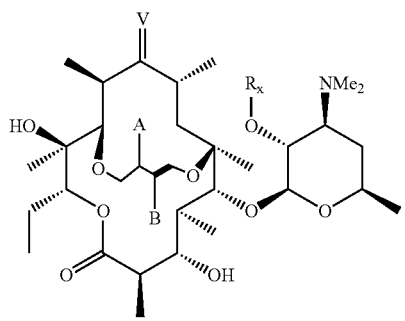

(XIV)

wherein A, B, $R_x$ and V are as previously defined.

A ninth preferred intermediate for the preparation of compounds represented by formula I is a compound represented by formula XV as illustrated below:

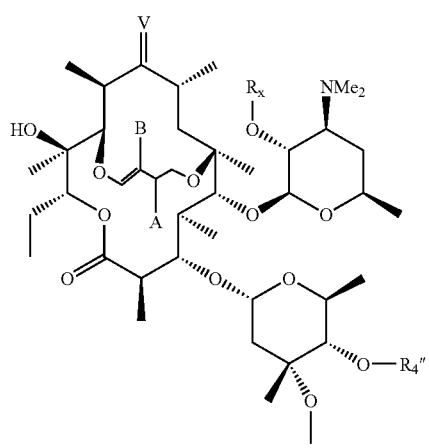

(XV)

wherein A, B, $R_x$, $R_4''$ and V are as previously defined.

A tenth preferred intermediate for the preparation of compounds represented by formula I is a compound represented by formula XVI as illustrated below:

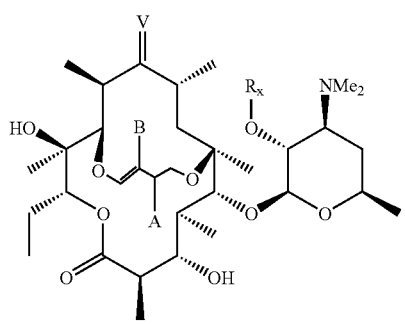

(XVI)

wherein A, B, $R_x$ and V are as previously defined.

An eleventh preferred intermediate for the preparation of compounds represented by formula I is a compound represented by formula XVII as illustrated below:

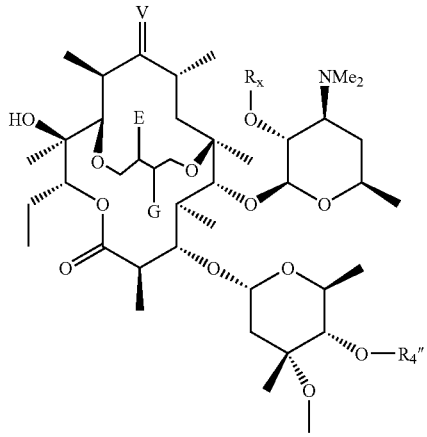

(XVII)

wherein E, G, V, $R_x$ and $R_4''$ are as previously defined.

A twelveth preferred intermediate for the preparation of compounds represented by formula I is a compound represented by formula XVIII as illustrated below:

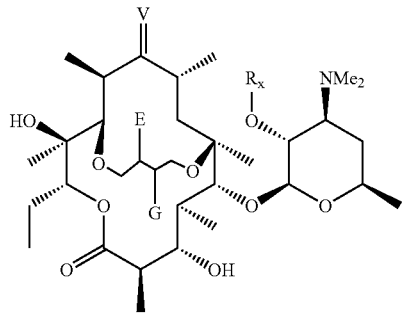

(XVIII)

wherein E, G, $R_x$ and V are as previously defined.

A thirteenth preferred intermediate for the preparation of compounds represented by formula I is a compound represented by formula XIX as illustrated below:

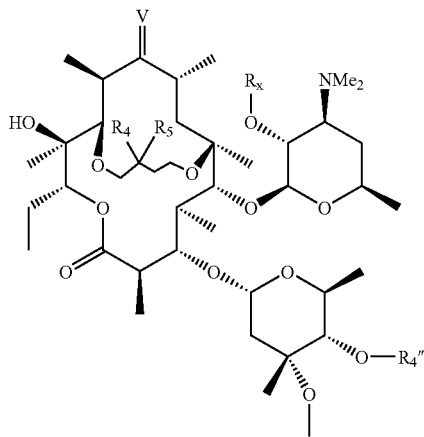

(XIX)

wherein V, $R_4$, $R_5$, $R_x$ and $R_4''$ are as previously defined.

A fourteenth preferred intermediate for the preparation of compounds represented by formula I is a compound represented by formula XX as illustrated below:

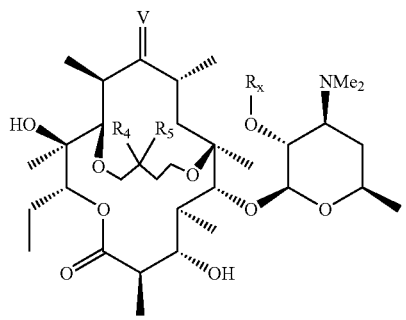

(XX)

wherein V, $R_4$, $R_5$ and $R_x$ are as previously defined.

A fifteenth preferred intermediate for the preparation of compounds represented by formula I is a compound represented by formula XXI as illustrated below:

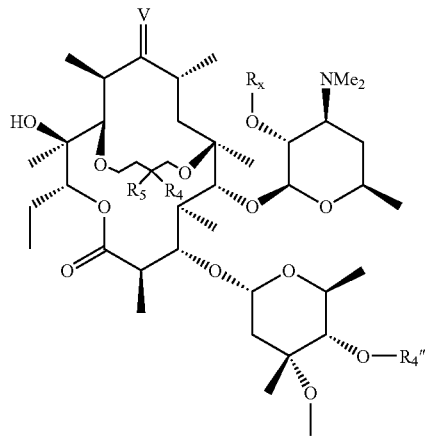

(XXI)

wherein V, $R_4$, $R_5$, $R_x$ and $R_4''$ are as previously defined.

A sixteenth preferred intermediate for the preparation of compounds represented by formula I is a compound represented by formula XXII as illustrated below:

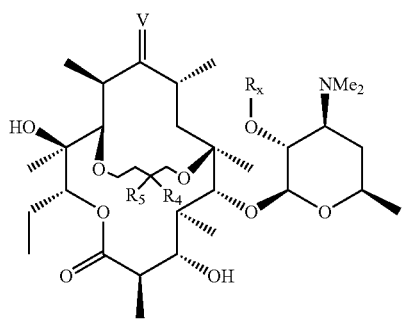

(XXII)

wherein V, $R_4$, $R_5$ and $R_x$ are as previously defined.

Compounds of formula (1-2) or (1-4), which are useful as the starting materials for the preparation of compounds of the present invention, may be synthesized as detailed in schemes 1 and 2 below. An erythromycin derivative (1-1) is prepared from erythromycin using the procedures described in U.S. Pat. Nos. 4,990,602; 4,331,803; 4,680,386; and 4,670,549 which are incorporated herein by reference. Also incorporated by reference is European Patent Application EP 260,938.

Scheme 1

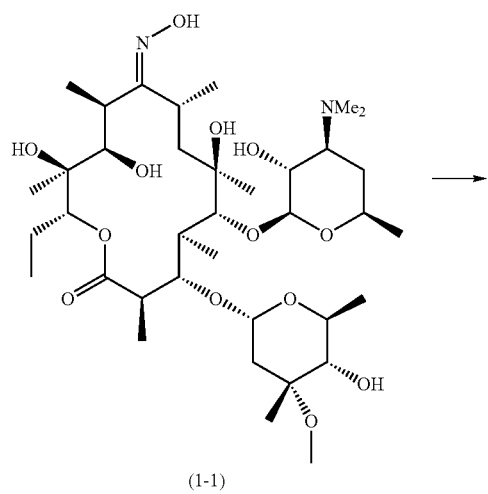

(1-1)

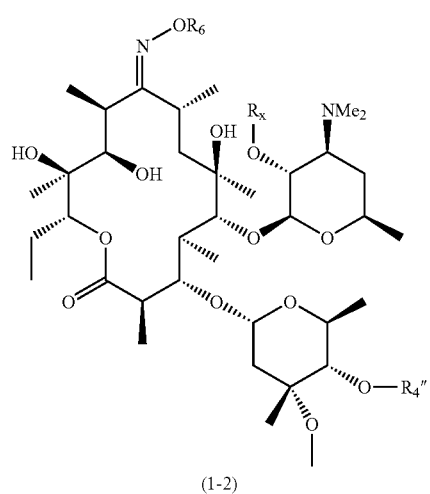

(1-2)

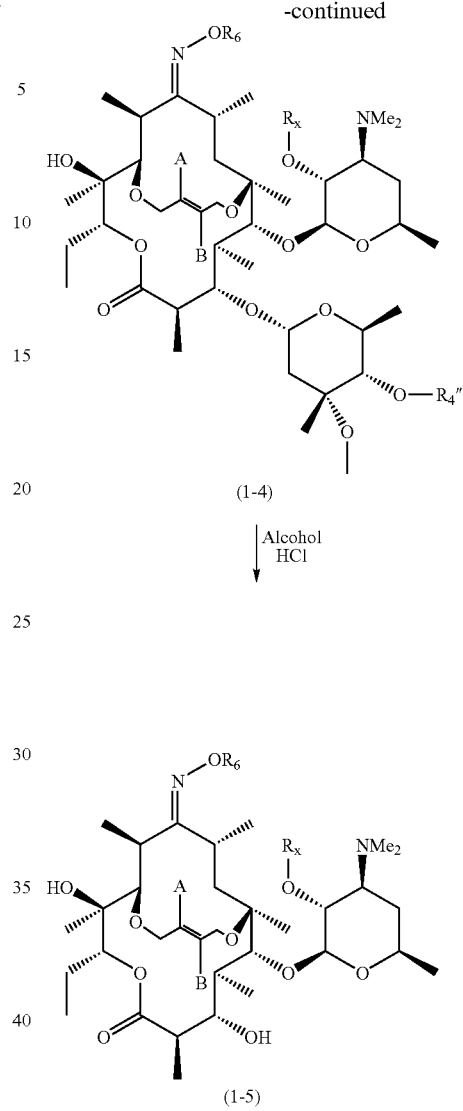

A synthetic method of the present invention, as illustrated in scheme 1, involves preparing a compound of formula (1-4) by reacting a compound of formula (1-2) with a suitable alkylating agent.

In accordance with scheme 1, the 9-keto group of the erythromycin backbone can be initially converted into an oxime by methods described in U.S. Pat. No. 4,990,602, followed by the protection of the 2'- and 4"-hydroxy groups with $R_x$ and $R_4''$ respectively, and if desired, the resulting oxime group can be further derivatized with $R_6$ to obtain the compounds of formula (1-2).

The 2'- and 4"-hydroxy groups are protected by reaction with suitable hydroxy group protecting agents in an aprotic solvent. Typical hydroxy group protecting reagents include, but are not limited to, acetylating agents, silylating agents, acid anhydrides, acid halides and the like. Examples of hydroxy group protecting reagents are, for example, acetyl chloride, acetic anhydride, benzoyl chloride, benzoic anhydride, benzyl chloroformate, hexamethyldisilazane, and trialkylsilyl chlorides.

Examples of aprotic solvents are dichloromethane, chloroform, tetrahydrofuran, N-methylpyrrolidinone, dimethylsulfoxide, N,N-dimethylformamide, N,N-dimethylacetamide, hexamethylphosphoric triamide, a mixture thereof or a mixture of one of these solvents with ether, tetrahydrofuran, 1,2-dimethoxyethane, 1,2-dichloroethane, acetonitrile, ethyl acetate, acetone and the like. Aprotic solvents do not adversely affect the reaction. Preferably, the solvent is selected from dichloromethane, chloroform, N,N-dimethylformamide, tetrahydrofuran, N-methylpyrrolidinone or mixtures thereof. A more thorough discussion of solvents and conditions for protecting the hydroxyl group can be found in T. W. Greene and P. G. M. Wuts, "Protective Groups in Organic Synthesis" 3$^{rd}$ ed., John Wiley & Son, Inc, 1999, which is incorporated by reference herein.

Protection of the 2'- and 4''-hydroxy groups may be accomplished sequentially or simultaneously to provide compound (1-2) where $R_x$ and/or $R_4$'' can be, for example, but not limited to, acetyl, benzoyl, trimethylsilyl, and the like. Preferred protecting groups include acetyl, benzoyl, and trimethylsilyl. A particularly preferred group for protecting the hydroxy and oxime groups is the acetyl protecting group, wherein $R_x=R_4''=R_6=$acetyl.

Acetylation of the hydroxy group is typically accomplished by treating the compound (1-1) with an acetylating reagent, for example, acetic anhydride or acetyl chloride.

The erythromycin derivative of formula (1-2) is then reacted with an alkylating agent of the formula:

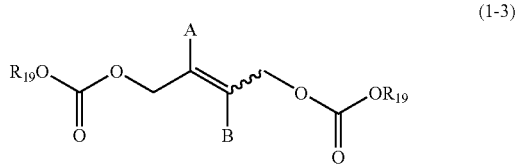

(1-3)

where $R_{19}$ is $C_1$–$C_{12}$-alkyl and A and B are as previously defined.

The reaction is carried out in an aprotic solvent with a palladium catalyst [Pd(0) or Pd(II)] with a phosphorus ligand such as, for example, dppb, dppe, and the like, in aprotic solvents from about room temperature to about 100° C., preferably at elevated temperature, for example, at or above 50° C., to provide compound (1-4) (see (a) Trost, B. M. Angew. Chem. Int. Ed. Eng. 1989, 28, 1179; (b) Heck, Palladium Reagents in Organic Synthesis, Academic Press: New York, 1985, Chapter 1; (c) Tsuji, Tetrahedron Lett. 1992, 33, 2987; (d) Beller et al. Angew. Chem. Int. Ed. Engl., 1995, 34 (17), 1848, etc.). Suitable aprotic solvents include, but are not limited to, tetrahydrofuran, N,N-dimethylformamide, dimethyl sulfoxide, N-methyl-2-pyrrolidone, hexamethylphosphoric triamide, 1,2-dimethoxyethane, methyl-tert-butyl ether, heptane, acetonitrile, isopropyl acetate and ethyl acetate. The most preferred solvents are tetrahydrofuran or toluene.

The palladium catalyst suitable in the present invention can be selected from, but not limited to, palladium (II) acetate, tetrakis (triphenylphosphine) palladium (0), tris (dibenzylideneacetone) dipalladium, tetradi(benzylideneacetone)dipalladium and the like. Palladium on carbon and palladium (II) halide catalysts are less preferred than other palladium catalysts for this process.

Suitable phosphorus ligands include, but are not limited to, triphenylphosphine, bis(diphenylphosphino)methane, bis(diphenylphosphino)ethane, bis(diphenylphosphino)propane, 1,4-bis(diphenylphosphino)butane, bis(diphenylphosphino)pentane, and tir(o-tolyl)phosphine, and the like.

The alkylating agents useful in the preparation of compounds of the present invention have the formula (1-3), as previously described. The preferred alkylating agents are those wherein $R_{19}$ is a tert-butyl, isopropyl or isobutyl group. The alkylating reagents are prepared by reaction of a di-ol with a wide variety of compounds for incorporating the di-carbonate moiety. The compounds include, but are not limited to, tert-butyl chloroformate, di-tert-butyl dicarbonate, 1-(tert-butoxycarbonyl) imidazole etc. The reaction is carried out in the presence of an organic or an inorganic base such as, for example, but not limited to, sodium hydroxide, sodium hydride, potassium hydride, potassium tert-butoxide, potassium hydroxide, ammonium hydroxide, sodium carbonate, potassium carbonate, ammonium carbonate, cesium fluoride, KHMDS, DMAP, pyridine, triethylamine, and the like, in an aprotic solvent such as THF, DMSO, DMF, dioxane, and the like, or mixtures thereof. The temperature for the reaction ranges from about –30° C. to about 60° C., preferably from about –30° C. to about 30° C.

The conversion of the di-ol into the dicarbonate can also be done by treating the di-ol with phosgene or triphosgene to prepare the chloroformate derivative of the di-ol. The di-chloroformate derivative is then converted into the di-carbonate by the methods described in Cotarca, L., Delogu, P., Nardelli, A., Sunijic, V, Synthesis, 1996, 553, incorporated by reference herein in its entirety. The reaction can be carried out in a variety of organic solvents such as dichloromethane, toluene, diethyl ether, ethyl acetate, chloroform, and the like, in the presence of a base as previously described herein. The temperature conditions can vary from about –30° C. to about 60° C. The reaction takes from about 1 hour to about 12 hours, preferably from about 2 to about 6 hours, to run to completion.

The cladinose moiety of macrolide (1-4) is removed either by mild acid hydrolysis or by enzymatic hydrolysis to give compounds of formula (1-5). Representative acids include, but are not limited to, hydrochloric acid, sulfuric acid, perchloric acid, chloroacetic acid, dichloroacetic acid, trifluoroacetic acid, and the like. Suitable solvents for the reaction include, but are not limited to, methanol, ethanol, isopropanol, butanol and the like. Reaction times range from about 0.5 hours to about 24 hours. The reaction temperature is preferably from about –10° C. to about 80° C.

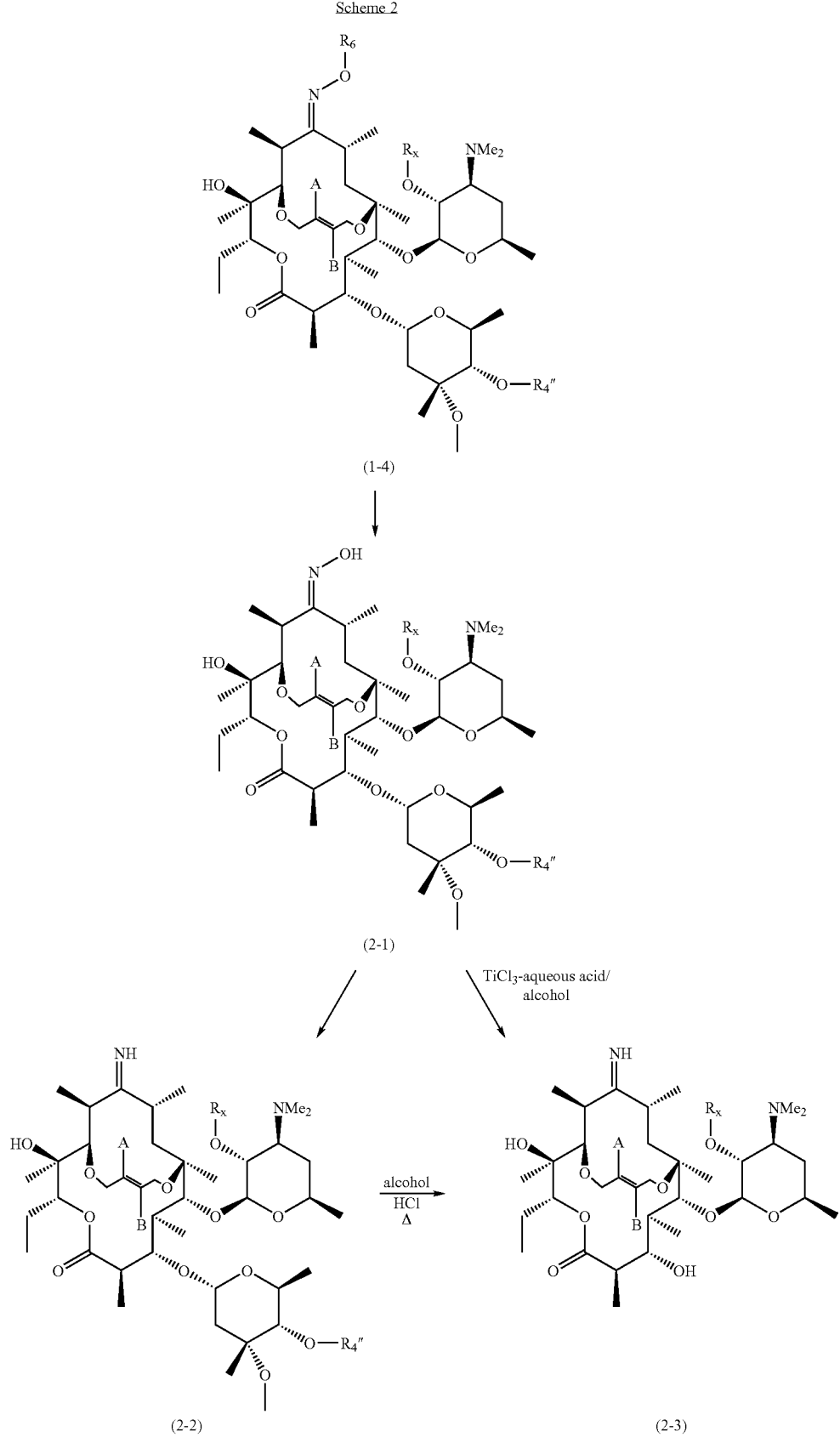

Compounds of formula (1-4) can be converted into the corresponding imine as outlined in scheme 2. Selective deprotection of the oxime (1-4) to compounds of the formula (2-1) is typically accomplished via alkaline hydrolysis in protic solvents. Representative alkali compounds include lithium hydroxide, sodium hydroxide, potassium hydroxide, and the like. Suitable solvents include, but are not limited to, tetrahydrofuran, 1,4-dioxane, 1,2-dimethoxyethane, isopropanol, ethanol, butanol and mixtures thereof. The reaction temperature is preferably from about 0° to about 35° C., and reaction time is preferably from about 0.5 hours to about 8 hours. Alternately, acid hydrolysis using an acid such as, but not limited to, hydrochloric acid, trifluoroacetic acid and the like, can be used to deprotect the oxime (1-4).

Deoximation of compounds of formula (2-1) under reducing conditions gives the macrolide imine of formula (2-2). Many reducing agents can be used to effect this transformation including, but not limited to, lithium aluminum hydride, titanium trichloride, sodium cyanoborohydride, borane, sodium nitrite, sulfur oxides such as, for example, sodium pyrosulfate, sodium thiosulfate, sodium sulfite, sodium hydrogensulfite, sodium metabisulfite, sodium dithionate, potassium thiosulfate, potassium metabisulfite, and the like (also see, (a) Greene (op. cit.); (b) J. March, *Advanced Organic Chemistry*, 4$^{th}$ ed., Wiley & Son, Inc., 1992, 9–51, and references therein). For example, when appropriate the reaction is carried out under acidic conditions in protic solvents. Representative acids include, but are not limited to, acetic acid, citric acid, oxalic acid, tartaric acid, formic acid, dilute hydrochloric acid, dilute phosphoric acid, dilute sulfuric acid, and the like. Suitable protic solvents include, but are not limited to, mixtures of water and methanol, ethanol, isopropanol, butanol etc.

Hydrolysis of the cladinose moiety can be accomplished as previously described in scheme 1 to give compounds of formula (2-3). Also, compounds of formula (2-3) can be formed by treating compounds of formula (2-1) with titanium trichloride (solution in aqueous acid) in an alcoholic solvent, for example, methanol, ethanol, and the like. The reaction can be carried out at elevated temperatures from about 50° C. to about 110° C. for about 1 to about 10 hours, or, at about room temperature for about 10 hours to about 24 hours.

Scheme 3

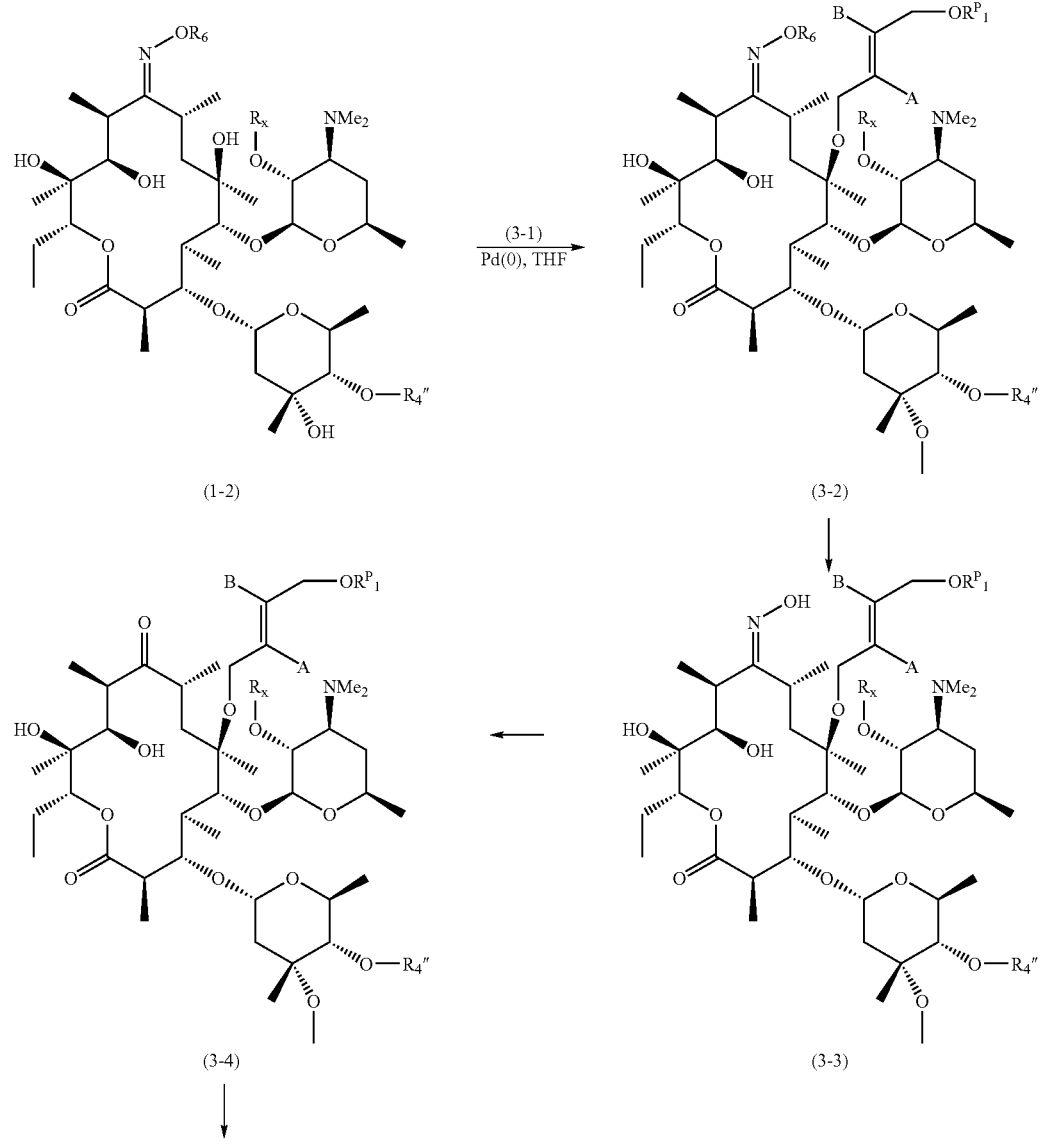

-continued

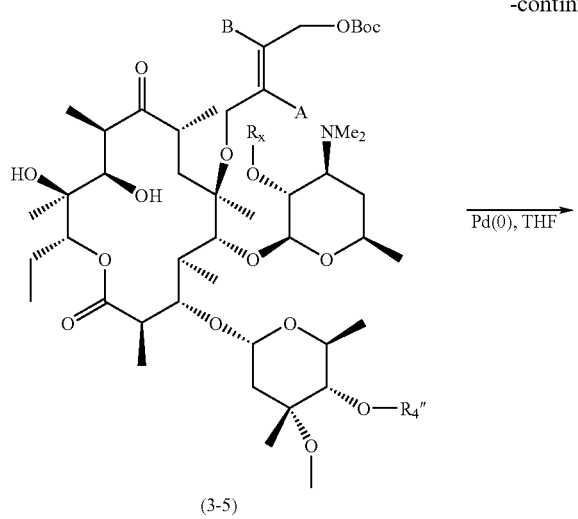

(3-5)

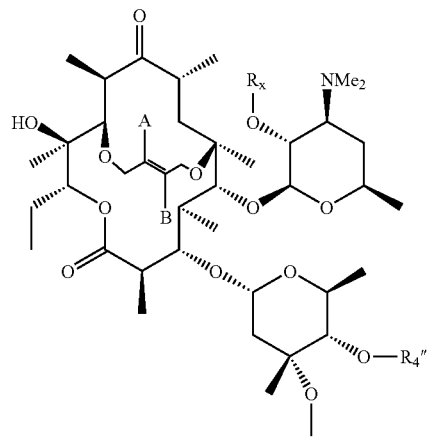

(3-6)

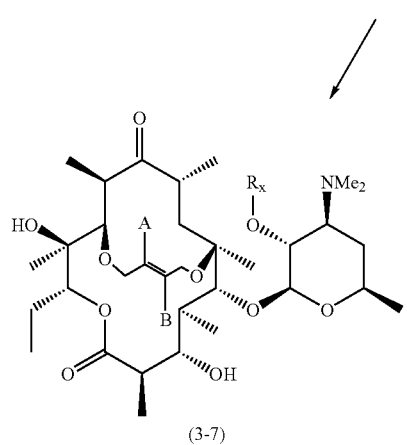

(3-7)

Stepwise formation of the 6,11-4-carbon bridged macrolides is also possible as outlined in scheme 3. In a similar manner as previously described, the procedure involves reacting a compound of formula (1-2) with a suitable alkylating agent. As before, the erythromycin derivative of formula (1-2) is reacted with an alkylating agent of the formula:

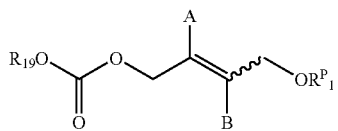

(3-1)

where $R_{19}$ is $C_1$–$C_{12}$-alkyl, A and B are as previously defined, and $R^P_1$ is H or $R^P$ where $R^P$ is as previously defined.

As discussed previously in scheme 1, compounds of formula (1-2) may be converted to compounds of formula (3-2) using a palladium catalyst with a phosphorous ligand in an aprotic solvent, preferably at elevated temperature, more preferably at or above 50° C. The preferred solvents are tetrahydrofuran and toluene.

The alkylating agents useful in the process of the invention are mixed silyl ether carbonates. Generally, the alkylating agents have the formula (3-1), as previously described. The preferred alkylating agents are those wherein $R_{19}$ is tert-butyl, isopropyl or isobutyl and $R^P$ is tert-butyl dimethyl silyl, triisopropyl silyl, tert-butyl diphenyl silyl or the like.

The alkylating reagents of formula (3-1) are prepared by reaction of a diol sequentially with a wide variety of compounds for incorporating the carbonate moiety, followed by a wide variety of compounds for incorporating the silyl moiety. Alkylating reagents include, but are not limited to, tert-butyl chloroformate, di-tert-butyl dicarbonate, and 1-(tert-butoxycarbonyl)imidazole; where as silylating reagents include, but are not limited to tert-butyl dimethyl silyl chloride, tert-butyl dimethyl silyl triflate, tert-butyl dimethyl silyl cyanide, and tert-butyl dimethyl silyl imidazole. Both reactions are carried out in the presence of an organic or an inorganic base as previously described in scheme 1. The temperature of the reactions varies from about −30° C. to about 30° C. Preferably, the alkylating reagent is di-tert-butyl dicarbonate and the silylating reagent is tert-butyl dimethyl silyl chloride.

The free oxime (3-3) is prepared using essentially the same procedure as for the deprotection of oxime (1-4) to (2-1) where $R_6$ is acetyl in scheme 2.

Reduction of oximes of formula (3-3) to the corresponding ketone compounds of formula (3-4) may be done by, for example, but not limited to, using a sulfite reducing agent, such as sodium hydrogensulfite, under acidic conditions, in protic solvents such as isopropanol, water etc., as previously described for the reduction of oximes of formula (2-1) to compounds of formula (2-2). Representative acids include, but are not limited to, acetic acid, citric acid, oxalic acid, tartaric acid, formic acid, dilute hydrochloric acid, dilute phosphoric acid, dilute sulfuric acid, and the like. Suitable protic solvents include, but are not limited to, mixtures of water and methanol, ethanol, isopropanol, butanol etc. The reaction is carried out at a temperature from about room temperature to about 110° C., preferably from about 50° C. to about 110° C., for about 1 to about 10 hours.

When the $R^p_1$, group is $R^P$ (i.e., a hydroxy protecting group) in a compound of formula (3-4) then the hydroxy protecting group is removed using appropriate conditions. For example, when the protecting group is a silyl group, TBAF, hydrofluoric acid or trifluoroacetic acid may be used (see, T. W. Greene and P. G. M. Wuts in *Protective Groups in Organic Synthesis* $3^{rd}$ ed., John Wiley & Son, Inc, 1999). The resulting primary hydroxy group (where $R^P_1$=H) is converted to the corresponding tert-butyl carbonate by standard methods known in the art, followed by alkylation of the 11-hydroxy group using a palladium (0) catalyst, as previously described in scheme 1, to form compounds of formula (3-6).

Removal of the cladinose sugar is accomplished as previously described in scheme 1 for converting compounds of formula (3-6) to compounds of formula (3-7).

where $R_3$ is as previously defined using standard acylating conditions to give compounds of formula (4-1). For example, imines of formula (2-3) can be acylated under basic conditions using a suitable acylating agent in an aprotic solvent, with or without an activation agent. Typical acylating agents include, but are not limited to, acetyl chloride, acetic anhydride, benzoyl chloride, benzoic anhydride, benzyl chloroformate, and the like. Examples of activation agents for acid coupling include, but are not limited to, DCC, EDC, 1-(3-dimethylaminopropyl)-3-ethyl-carbodiimide hydrochloride etc.

Typical bases useful in acylation reactions include, but are not limited to, DMAP, pyridine, triethylamine, diisopropyl ethylamine, N-methyl morpholine, N-methyl pyrrolidine, 2,6-lutidine, 1,8-diazabicyclo[5.4.0]undec-7-ene, and the like (see, T. W. Greene and P. G. M. Wuts in "Protective Groups in Organic Synthesis" $3^{rd}$ ed., John Wiley & Son, Inc, 1999, and references therein). If required, compounds of formula (2-3) can be further deprotected as described in scheme 1 to obtain the 2' free hydroxy group and the 9-position oxime.

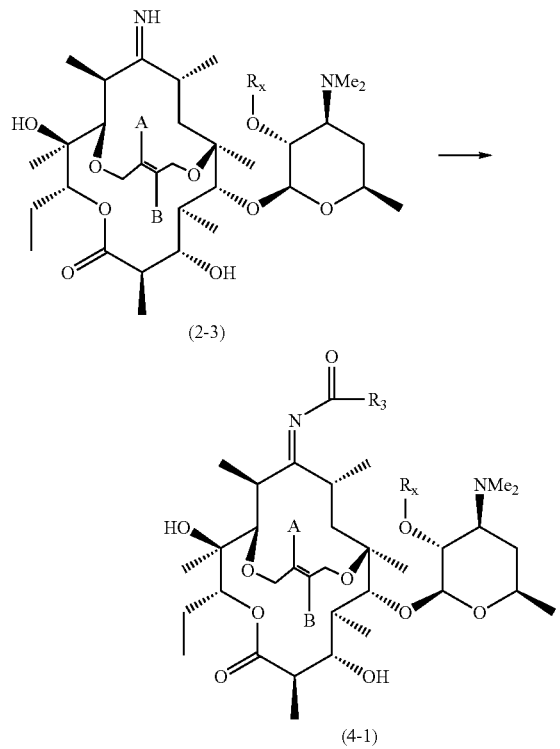

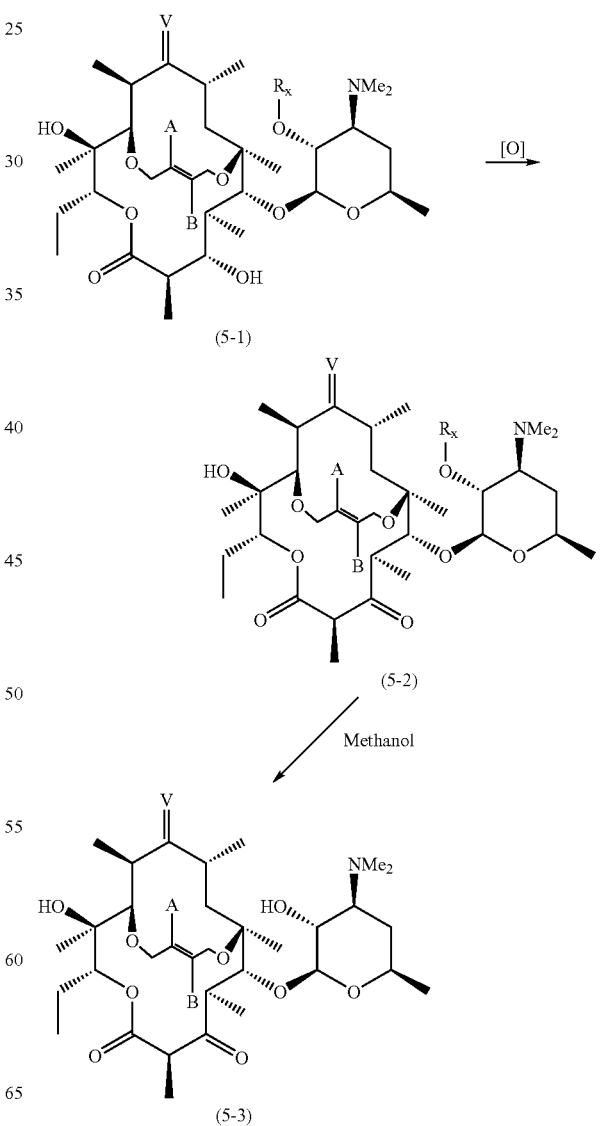

The imine in the 9 position of compounds of formula (2-3) can be acylated with an acylating agent such as, for example, $R_3C(O)T$, where T is a halogen or OH, or $(R_3C(O))_2O$, Compounds according to the invention (5-2) may be prepared by oxidation of the secondary alcohol in compounds of the formula (5-1) using an oxidizing agent (such as, but not limited to, 1,1,1-triacetoxy-1,1-dihydro-1,2-benziodoxol-3(1H)-one ("Dess-Martin reagent"), NCS/Me$_2$S, TPAP/NMO, PCC, PDC, sulfur trioxide pyridine complex in DMSO, or oxalyl chloride in DMSO, and the like (see, J. March, *Advanced Organic Chemistry* 4$^{th}$ ed., Wiley & Son, amine, for example, propylamine, butylamine, and the like. Alcoholic solvents preferred for the deprotection are methanol and ethanol. A more thorough discussion of the procedures, reagents and conditions for removing protecting groups is described in literature, for example, by T. W. Greene and P. G. M. Wuts in "Protective Groups in Organic Synthesis" 3$^{rd}$ ed., John Wiley & Son, Inc, 1999, which is incorporated by reference herein.

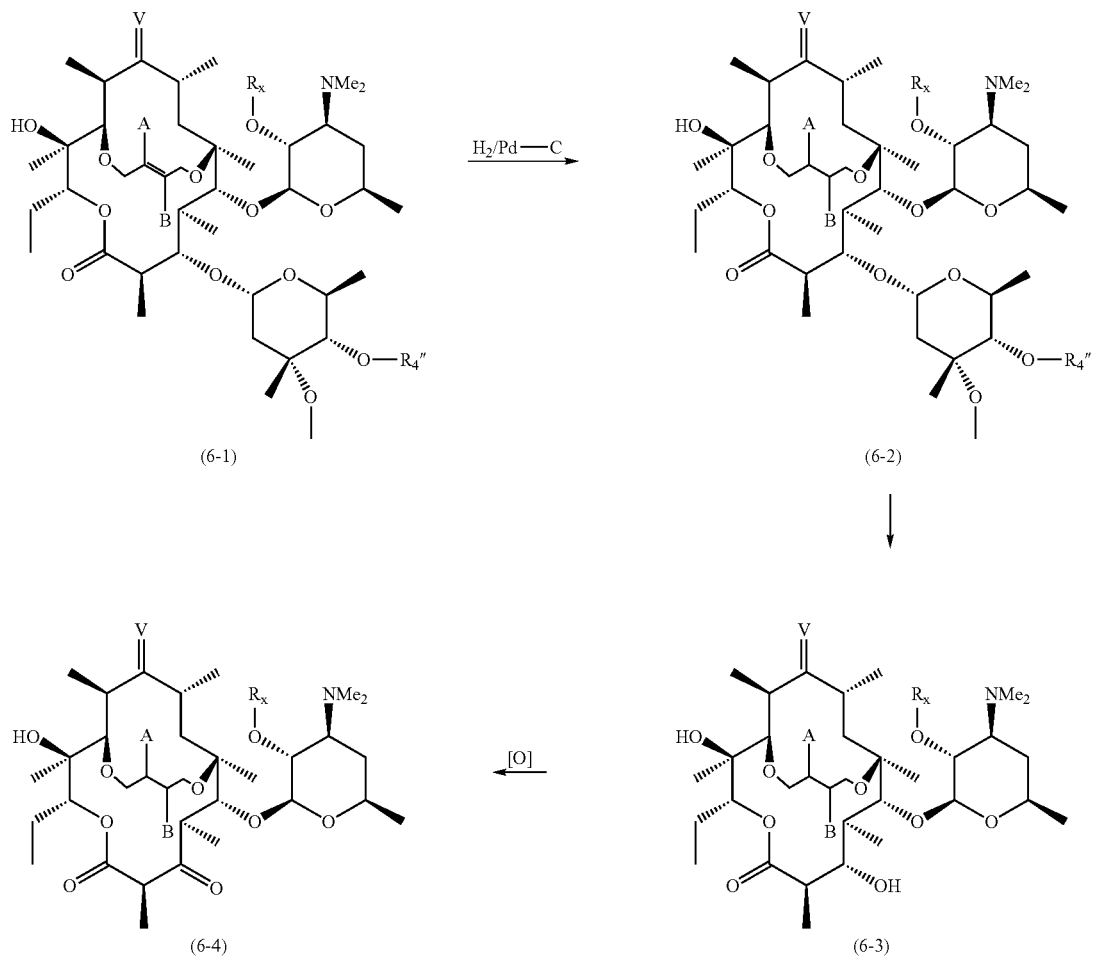

Scheme 6

Inc., 1992, and the references therein) in an aprotic solvent such as methylene chloride, ethylene chloride, THF, chloroform, DMF, acetonitrile or the like at a temperature from about 0° C. to about 50° C. for about 1 to about 48 hours.

Compounds of formula (5-2) can be further deprotected to give a free hydroxy group at the 2' position, compounds of formula (5-3), by treating with methanol at a temperature from about room temperature to about reflux temperature. Simultaneous deprotection, of both the oxime and the 2' hydroxy group, can be accomplished similarly.

Conditions for deprotection include, but are not limited to, treating with an alcoholic solvent from room temperature to reflux, or treatment with an amine, preferably a primary Compounds according to the formula (6-2) may be prepared from compounds of formula (6-1) by selective hydrogenation methods known in the art, for example, but not limited to, metal hydrides, such as, borane, or hydrogen in the presence of a catalyst, such as, palladium-on-charcoal, platinum metal or oxide, Wilkinson's catalyst and the like (see, Rylander, *Hydrogenation Methods*; Academic Press: New York, 1985; J. March, *Advanced Organic Chemistry* 4$^{th}$ ed., Wiley & Son, Inc., 1992; and the references therein). Compounds according to the formula (6-4) may be prepared by removal of the cladinose sugar from compounds according to formula (6-2), as described in scheme 1, and subsequently oxidizing compounds according to formula (6-3), as previously described in scheme 5.

Scheme 7

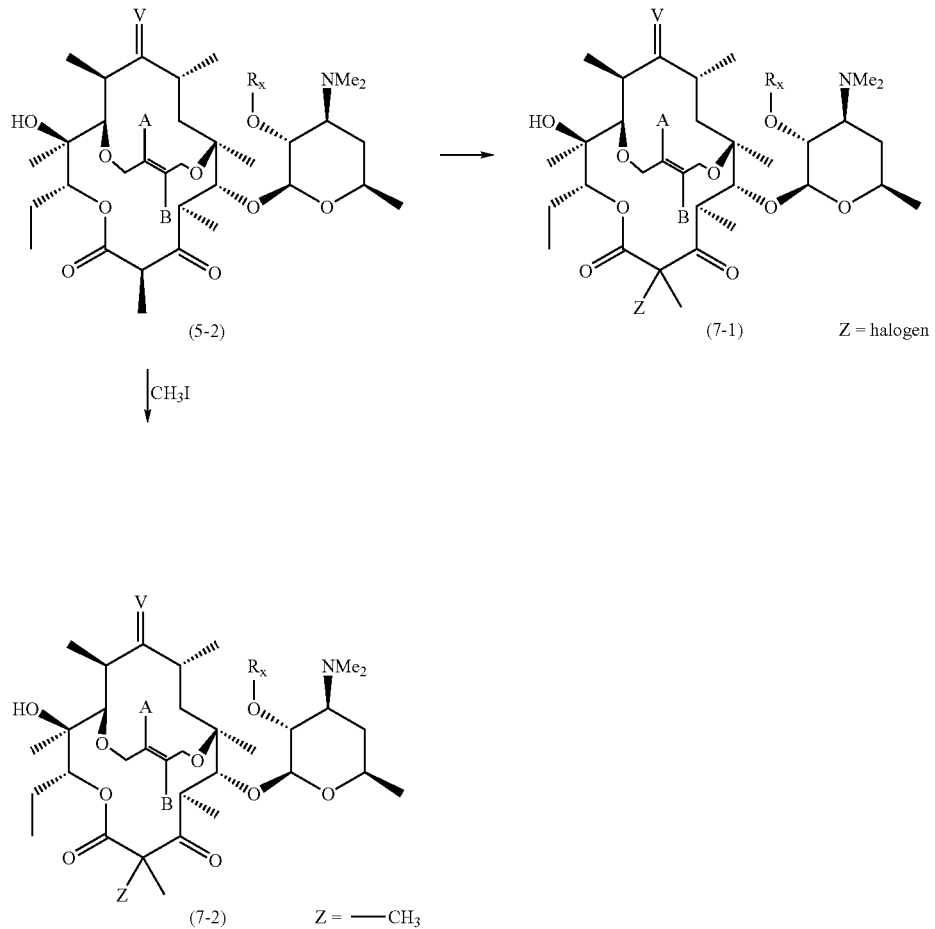

Scheme 7 illustrates the procedure by which compounds of formula (5-2) may be converted to compounds of formula (7-1) and (7-2) by undergoing a substitution reaction at the C-2 position of the compounds of the present invention.

Compounds of formula (5-2) can be halogenated to form compounds of formula (7-1) by the process in U.S. Pat. No. 6,124,269 and WO 00/62783 which are herein incorporated by reference in their entirety. Various halogenating reagents suitable in this procedure are as described below. Fluorinating reagents include, but are not limited to, N-fluorobenzenesulfonimide in the presence of a base, 10% $F_2$ in formic acid, 3,5-dichloro-1-fluoropyridinium tetrafluoroborate, 3,5-dichloro-1-fluoropyridinium triflate, $(CF_3SO_2)_2NF$, N-fluoro-N-methyl-p-toluenesulfonamide in the presence of base, N-fluoropyridinium triflate, N-fluoroperfluoropiperidine in the presence of base. Chlorinating reagents include, but are not limited to, hexachloroethane in the presence of base, $CF_3CF_2CH_2ICl_2$, $SO_2Cl_2$, $SOCl_2$, $CF_3SO_2Cl$ in the presence of base, $Cl_2$, NaOCl in the presence of acetic acid. Brominating reagents include, but are not limited to, $Br_2 \cdot$pyridine$\cdot$HBr, $Br_2$/acetic acid, N-bromosuccinimide in the presence of base, LDA/BrCH$_2$CH$_2$Br, or LDA/CBr$_4$. Suitable iodinating reagents for example are N-Iodosuccinimide in the presence of base, or $I_2$ etc. A preferred halogenating reagent is N-fluorobenzenesulfonimide in the presence of sodium hydride.

Suitable bases for the halogenation reactions include, but are not limited to, alkali metal hydrides, such as NaH and KH, or amine bases, such as LDA or triethylamine, and the like. A preferred halogenating reagent is N-fluorobenzenesulfonimide in the presence of sodium hydride.

Suitable solvents are DMF, DMSO, pyrrolidinone and the like.

Alternatively, the C-2 position of compounds of formula (5-2) can be methylated by treatment with methyl iodide in the presence of a base such as $K_2CO_3$, NaOH and the like, with or without a phase transfer catalyst such as tetrabutylammonium iodide, and the like, in THF, methylene chloride, DMF, DMSO, water and the like or combinations thereof, at from about 0° C. to about 50° C. for 1–24 hours to provide compounds of formula (7-2). Both compounds of formula (7-1) and (7-2) can be deprotected upon treatment with methanol to remove the $R_x$ protecting group.

It will be appreciated by one skilled in the art that the compound of formula (5-2) can be substituted by other compounds of the present invention to obtain the corresponding C-2 halogenated or methylated product when desired.

Scheme 8

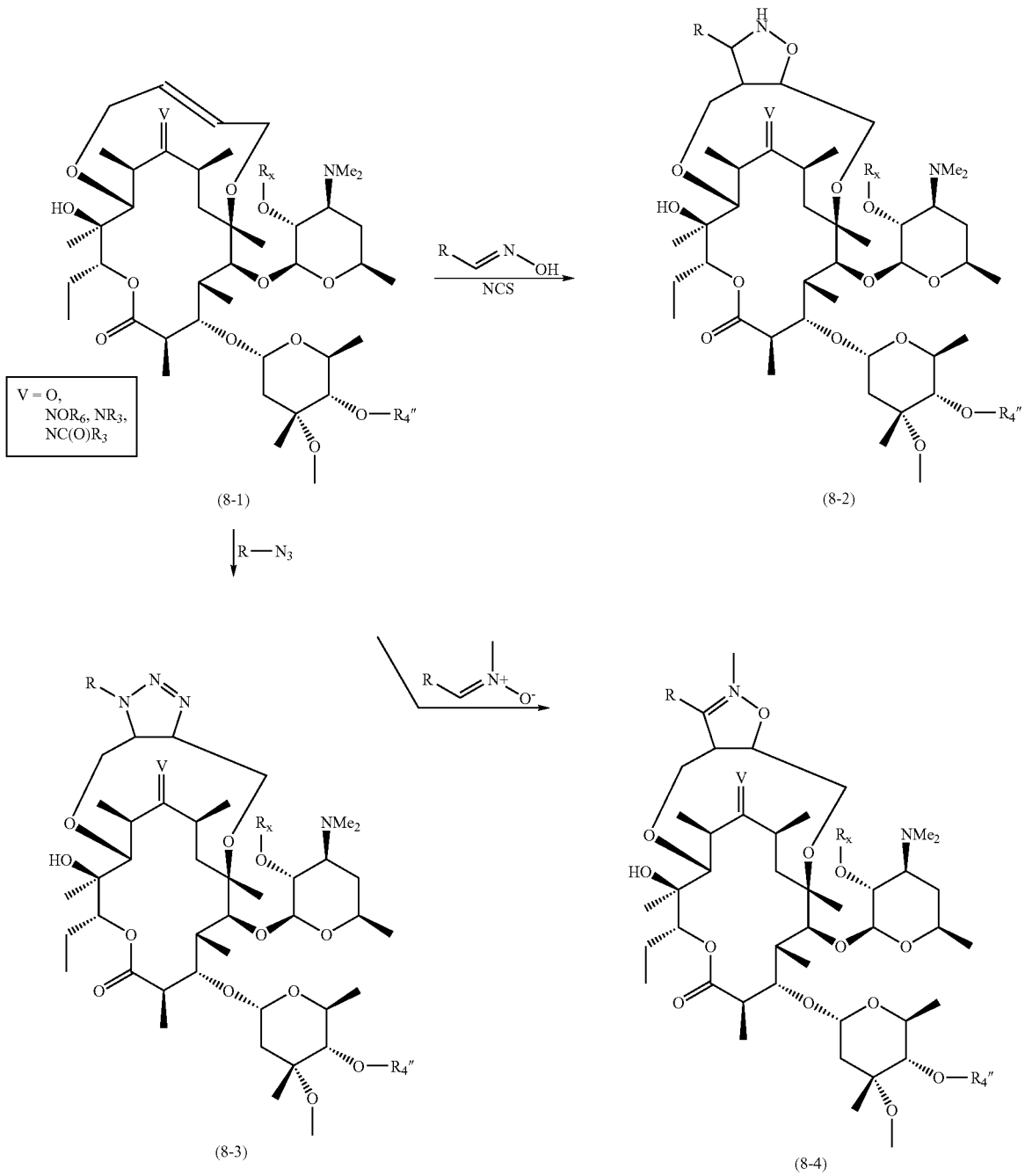

Compounds (8-2, 8-3 and 8-4, where R is $R_3$ as previously defined herein) can be prepared by the well-established 1,3-dipolar cycloaddition reactions, such as, but not limited to, reaction of compound (8-1) and an oxime in the presence of NCS in an aprotic solvent such as ethyl acetate, methylene chloride, THF, or the like, to form compound (8-2) (see (a) Tufariello, Joseph J. *Nitrones* in 1,3 *[One,Three]-Dipolar Cycloaddit. Chem.* (1984), 2, 83–168. (b) Huisgen, Rolf. 1,3-*Dipolar cycloaddition—introduction, survey, mechanism* in 1,3 *[One,Three]-Dipolar Cycloaddit. Chem.* (1984), 1, 1–176, and the references therein). Compounds (8-3) and (8-4) can be prepared similarly by reacting compound (8-1) with an azide or a nitrone respectively.

Other 1,3-Dipolar cycloaddition reactants useful in forming cycloaddition products with compounds of the present invention such as compound (8-1) include, but are not limited to, diazoalkane, nitrous oxide, nitrile imine, nitrile ylide, nitrile oxide, etc. (see, Padwa 1,3-*Dipolar Cycloaddition Chemistry*, 2 vols.; Wiley: New York, 1984, and J. March, *Advanced Organic Chemistry*, 4$^{th}$ edition; Wiley: New York, 1992, and the references therein).

Scheme 9

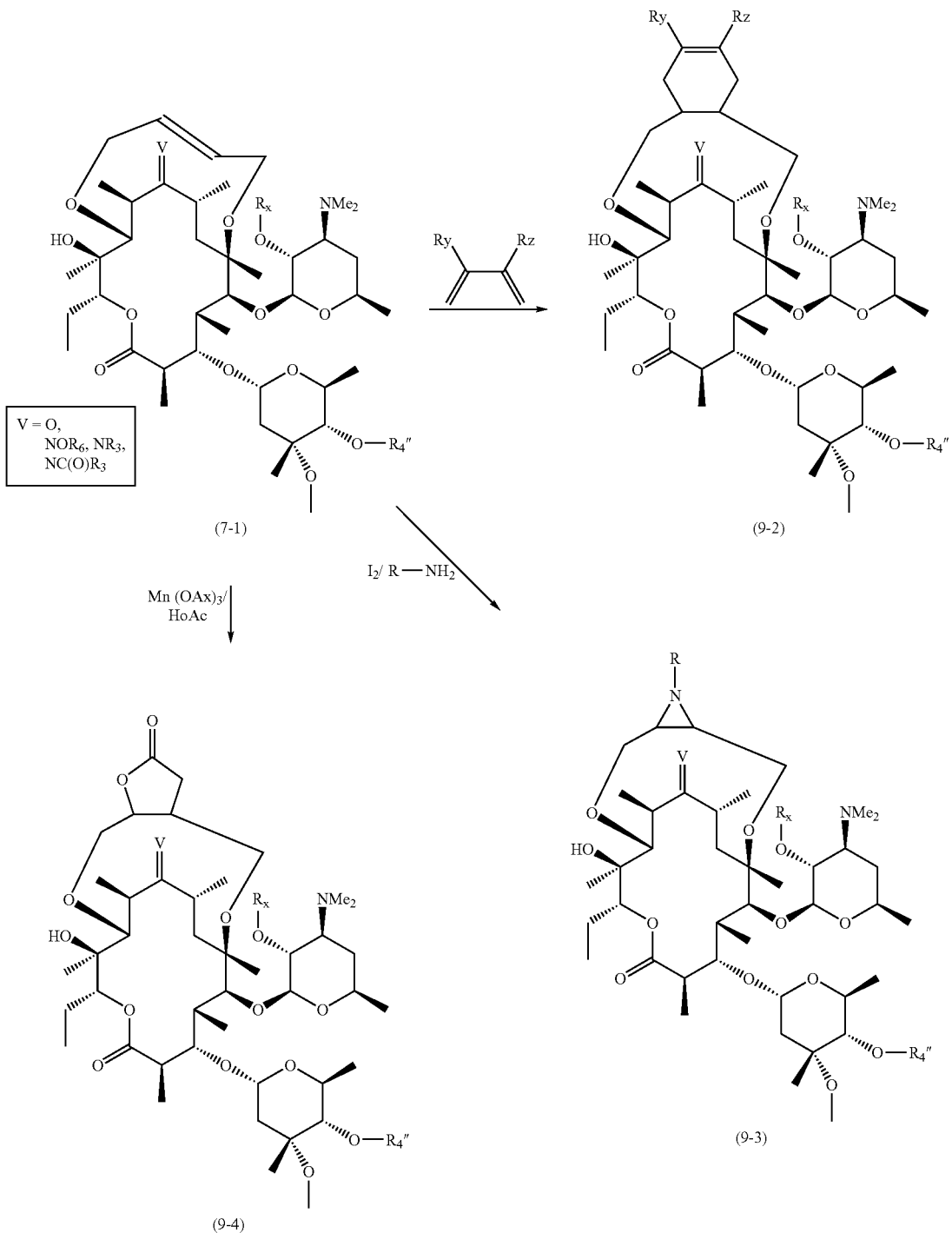

Compound (9-2) is prepared by Diels-Alder reactions, where $R_y$ and $R_z$ are for example, but not limited to, CHO, COOH, COOR, COR, COAr, CN, $NO_2$, Ar, $CH_2OH$, $CH_2Cl$, $CH_2NH_2$, $CH_2CN$, $CH_2COOH$, halogen, —C≡C—, R and the like, R being $R_3$ as previously defined herein (see (a) Danishefsky, Samuel. *Cycloaddition and cyclocondensation reactions of highly functionalized dienes: applications to organic synthesis in Chemtracts: Org. Chem.* (1989), 2 (5), 273–97, (b) Larock *Comprehensive Organic Transformation*; VCH: New York, 1989, 263–272, and the references therein).

Aziridines such as compound (9-3) can be obtained from, for example, but not limited to, the reaction of compound (7-1) with iodine in the presence of a primary amine in an aprotic solvent such as methylene chloride, THF, and the like.

Lactones such as compound (9-4) can be obtained by a variety of reactions such as but not limited to, reaction with: manganese (III) acetate in the presence of acetic acid, lead tetraacetate, α-bromocarboxylic acids in the presence of benzoyl peroxide etc. (see, Larock *Comprehensive Organic Transformation*; VCH: New York, 1989; J. March, *Advanced Organic Chemistry*, 4$^{th}$ edition; Wiley: New York, 1992, and the references therein).

about 3 equivalents of NMO in a solvent like t-butanol or acetone, with or without water, in the presence of about 1 to about 10% of $OsO_4$. Compound (10-3) can then be obtained from compound (10-2) through standard acylation or alkylation of the diol, where $R_7$ and $R_8$ are independently selected from $R_3$ and where $R_3$ is as previously defined herein.

Compound (10-4) is prepared by epoxidation of the double bond with reagents such as, but not limited to,

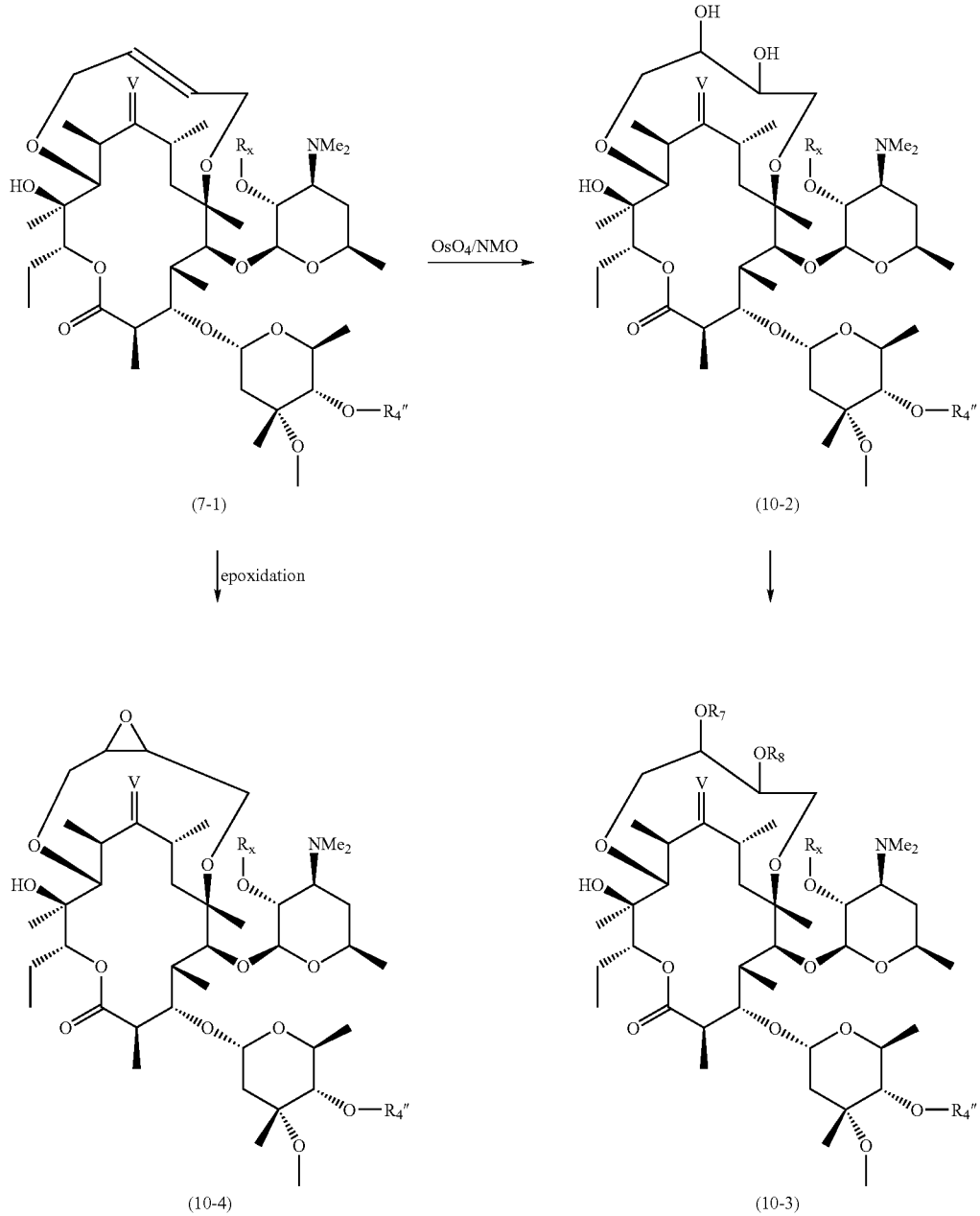

Compound (10-2) is prepared by osmium tetraoxide ($OsO_4$) catalyzed dihydroxylation of the double bond. In a typical procedure, compound (7-1) is treated with about 1 to peracids, e.g. m-CPBA, hydrogen peroxide, t-BuOOH etc. (see (a) *Chem. Rev.* 1989, 89, 431; (b) *Chem. Rev.* 1992, 92, 873, and references therein).

Scheme 11

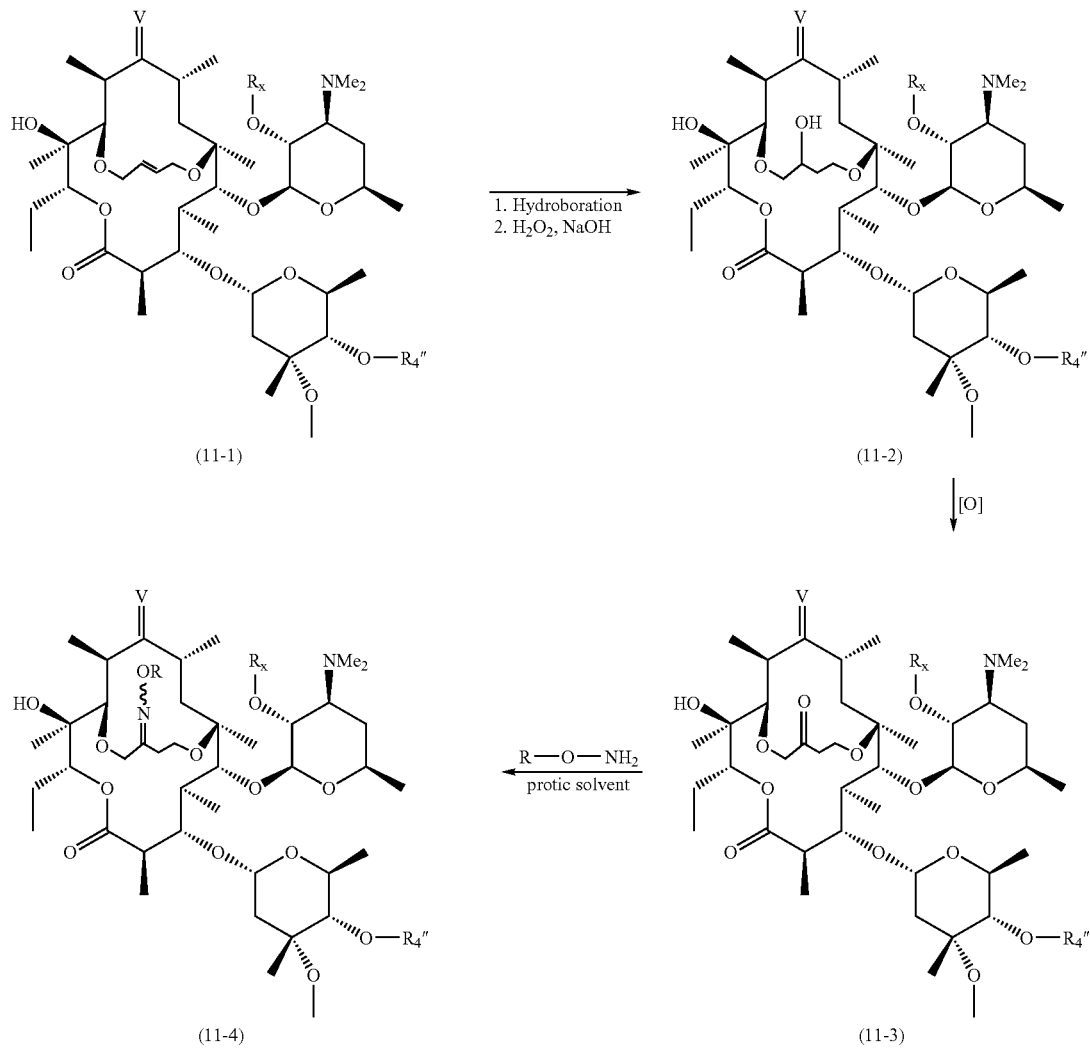

Compounds of formula (11-1) can be converted to compounds of formula (11-2) by, for example, but not limited to, hydroboration with a borane reagent, for example, $B_2H_6$-THF, 9-BBN (9-borabicyclo[3.3.1]nonane), and the like, (optionally complexed with THF, dimethylsulfide, phosphines, tertiary amines etc.) and followed by treatment with hydrogen peroxide and NaOH, to obtain compounds of formula (11-2).

Compounds of formula (11-2) may be oxidized to compounds of formula (11-3) with a suitable oxidizing agent as previously mentioned in scheme 5. Compounds of formula (11-3) can be reacted with appropriate substituted hydroxylamines of the general formula $RONH_2$ where R is preferably $R_3$, where $R_3$ is as previously defined, in a protic solvent under acidic or basic conditions to give compounds of the formula (11-4). Representative acids include, but are not limited to, hydrochloric acid, phosphoric acid, sulfuric acid, p-toluenesulfonic acid, etc. Representative bases include, for example, triethylamine, pyridine, diisopropylethyl amine, 1,5-lutidine, and the like. Appropriate solvents include, but are not limited to, methanol, ethanol, water, tetrahydrofuran, 1,2-dimethoxyethane and ethyl acetate.

Also, ketone compounds of the formula (11-3), where the ketone is on the 6,11-4-carbon bridge, may be further derivatized, for example, but not limited to, conversion to the corresponding amines by reductive amination, reaction with hydrazines to form the corresponding hydrazones, conversion to substituted alkenes by Wittig reaction, alkylation with Grignard reagent etc., by standard methods known in the art and from references incorporated herein.

The cladinose moiety in compounds prepared according to schemes 8–11 may be removed according to the procedure described in scheme 1 and the corresponding ketolide compound may be obtained by the procedure described in scheme 5.

Alternately, the double bond in the 6,11-4-carbon bridge in compounds of formula (5-3) may be further derivatized by appropriate procedures known in the art and as disclosed herein, for example, but not limited to, Diels-Alder reactions, 1,3-dipolar cycloaddition reactions, hydrogenation, reaction with primary amines in the presence of iodine to form aziridines, hydroboration, etc.

EXAMPLES

The compounds and processes of the present invention will be better understood in connection with the following examples, which are intended as an illustration only and are not limiting of the scope of the invention. Various changes and modifications to the disclosed embodiments will be apparent to those skilled in the art, and such changes and modifications including, without limitation, those relating to the chemical structures, substituents, derivatives, formulations and/or methods of the invention may be made without departing from the spirit of the invention and the scope of the appended claims.

Although the invention has been described with respect to various preferred embodiments, it is not intended to be limited thereto, but rather those skilled in the art will recognize that variations and modifications may be made therein which are within the spirit of the invention and the scope of the appended claims.

Example 1

Compound of Formula (I): W=—$CH_2CH$=$CHCH_2$—; X and Y taken together with the carbon atom they are attached to =C=$NC(O)CH_3$; L=$CH_2CH_3$; Z=H and $R_x$=H.

Step 1a: Compound of Formula (VII): $R_6$=$C(O)_6H_5$, $R_4''$=$C(O)C_6H_5$ and $R_x$=$C(O)C_6H_5$;

A solution of erythromycin A oxime (27.5 g, 36.7 mmol), benzoic anhydride (34.9 g, 154 mmol) in 200 ml THF was added to triethylamine (22.5 ml, 161.6 mmol) and DMAP (4.49 g, 36.7 mmol) at room temperature and stirred for 24 hrs. The reaction mixture was condensed to ~100 ml. Then 300 ml of ethyl acetate was added and washed with sat. $NaHCO_3$ (300 ml×3) and brine (300 ml×1). The organic phase was dried on anhydrous sodium sulfate and the solvent was removed in vacuo. To this second residue was added hexane (100 ml) and the solvent was removed in vacuo. This procedure (addition of hexane and concentration in vacuo) was repeated 3 times. The resulting white foam residue was dried in vacuo to afford the product (~90 g).

MS (ESI) m/z=1062.27 $(M+H)^+$.

Step 1b: Compound of Formula (VIII): A=B=H, V taken together with the carbon atom it is attached to =C=N—O—$C(O)C_6H_5$, $R_4''$=$C(O)C_6H_5$ and $R_x$=$C(O)C_6H_5$;

A mixture of the compound from step 1a (5.31 g, 5 mmol), 2-butene, 4-[bis-(tert-butyl)carbonate] (4.3 g, 15 mmol) and 1,4-bis(diphenylphosphino)-butane (213 mg, 0.5 mmol) was dissolved in freshly distilled THF (250 ml). To the solution was added $Pd_2(dba)_3$ (229 mg, 0.25 mmol). The reaction mixture was heated to reflux slowly. After refluxing for 14 hours, the reaction was cooled to room temperaure, diluted with 400 ml ethyl acetate, and washed with saturated $NaHCO_3$ (400 ml) and brine (400 ml). The organic phase was dried over $Na_2SO_4$, the solvent was removed in vacuo and the solid residue was purified by silica gel chromatography (acetone:hexane/1:2) to give the title compound (5.0 g).

MS (ESI) m/z=1114.82 $(M+H)^+$.

Step 1c: Compound of Formula (VIII): A=B=H, V taken together with the carbon atom it is attached to =C=N—OH, $R_4''$=$C(O)C_6H_5$ and $R_x$=H;

A solution of the compound from Step 1b (22 g) in 400 ml methanol is refluxed for 48 hours. The solvent is removed in vacuo and the compound is purified by column chromatography ($CH_2Cl_2$: 2M ammonia in MeOH/95:5) to give the title compound (18.5 g).

Step 1d: Compound of Formula (IX): A=B=H, V taken together with the carbon atom it is attached to =C=NH and $R_x$=H;

Titanium trichloride (20% in 3% hydrochloric acid) is added dropwise for 10 minutes into a stirred solution of the compound from Step 1c and ammonium acetate (17.4 g, 226 mmol) in 120 ml of methanol at 0° C. The reaction mixture is allowed to warm up to room temperature and stirred overnight. The pH of the reaction mixture is adjusted to pH=10 by slow addition of 3N aqueous sodium hydroxide. The aqueous solution is extracted with ethyl acetate (200 ml) and the organic phase is washed once with saturated sodium bicarbonate (200 ml), dried over sodium sulfate and the solvent is removed in vacuo. The residue is purified by silica gel chromatography ($CH_2Cl_2$: 2M ammonia in methanol/95:5) to give the title compound (3.0 g).

Step 1e: Compound of Formula (IX): A=B=H, V taken together with the carbon atom it is attached to =C=$NC(O)CH_3$ and $R_x$=$C(O)CH_3$;

Acetic anhydride (1.36 ml, 14.4 mmol) is added into a solution of the title compound of step 1d (3 g, 4.8 mmol) and triethylamine (2.8 ml, 20 mmol) in dichloromethane (40 ml). The reaction mixture is stirred at room temperature for 4 hours, diluted with 100 ml of dichloromethane and washed with saturated sodium bicarbonate (3×100 ml) and brine (100 ml). The organic phase is dried over sodium sulfate and the solvent is removed in vacuo. The residue is purified by silica gel chromatography (hexanes:acetone/1:1) to give the title compound (2.9 g).

Step 1f: Compound of Formula (II): A=B=H, X and Y taken together with the carbon atom they are attached to =C=$NC(O)CH_3$, Z=H and $R_x$=$C(O)CH_3$;

To a solution of compound from Step 1e (2.9 g, 4.08 mmol) in 40 ml dichloromethane is added Dess-Martin reagent (1.9 g, 4.5 mmol) at room temperature. The mixture is stirred at room temperature for 2 hours. The reaction is quenched with sodium bicarbonate (50 ml) and $Na_2S_2O_3$ (2 g). The organic phase is separated and washed with brine (50 ml). The solvent is removed in vacuo and the residue is purified on chromatography (Hexane:Acetone/1:1) to give the title compound.

Step 1g: Compound of Formula (I): W=—$CH_2CH$=$CHCH_2$—, X and Y taken together with the carbon atom they are attached to =C=$NC(O)CH_3$, L=$CH_2CH_3$, Z=H and $R_x$=H;

A solution of compound from Step 1f (2.0 g, 2.82 mmol) in 40 ml methanol is refluxed for 5 hours. The solvent is evaporated to give the title compound.

Example 2

Compound of Formula (I): W=—$CH_2CH$=$CHCH_2$—; X and Y taken together with the carbon atom they are attached to =C=NH; L=$CH_2CH_3$; Z=H and $R_x$=H;

Potassium carbonate (50 mg) is added to a solution of compound of step 1g in methanol (6 ml). The mixture is stirred at room temperature for 3 days. The solvent is removed on vacuo and the residue is purified on chromatography ($CH_2Cl_2$: 2M ammonia in methanol/95:5) to give title compound.

Example 3

Compound of Formula (I): W=—CH$_2$CH=CHCH$_2$—; X and Y taken together with the carbon atom they are attached to =C=N—OCH$_2$OCH$_3$; L=CH$_2$CH$_3$; Z=H and R$_x$=H.

Step 3a: Compound of Formula (IX): A=B=H, V taken together with the carbon atom it is attached to =C=N—OH and R$_x$=C(O)C$_6$H$_5$;

To a solution of compound from step 1b (4.2 g, 4.5 mmol) in 50 ml methanol is added 2M HCl (10 ml). The reaction mixture is refluxed for 1.5 hours and then concentrated in vacuo to 30 ml, diluted with saturated NaHCO$_3$(30 ml), extracted with ethyl acetate (50 ml) and dried over Na$_2$SO$_4$. The solvent is evaporated in vacuo and the residue is purified by silia gel chromatography (Hexane:Acetone/1:1) to give the title compound.

Step 3b: Compound of Formula (IX): A=B=H, V taken together with the carbon atom it is attached to =C=N—OCH$_2$OCH$_3$ and R$_x$=C(O)C$_6$H$_5$;

To a solution of compound from step 3a (6.85 g, 10 mmol) in 40 ml DMF at 0° C. was added NaH (303 mg, 1.3 mmol) in portions. After 10 minutes, MOMCl (900 μl, 1.15 mmol) was added at 0° C. during 15 minutes. The mixture was stirred at room temperature for 16 hours and quenched with saturated NaHCO$_3$ (60 ml). The product was extracted with ethyl acetate (60 ml) and dried over Na$_2$SO$_4$. The solvent was evaporated in vacuo and the residue was purified by silica gel chromatography (Hexane:Acetone/1:1) to give the title compound (4.5 g).

MS (ESI) m/z=729 (M+H)$^+$.

Step 3c: Compound of Formula (IX): A=B=H, V taken together with the carbon atom it is attached to =C=N—OCH$_2$OCH$_3$ and R$_x$=C(O)C$_6$H$_5$;

To a solution of compound from step 3b (4.4 g, 6 mmol) in 50 ml dichloromethane is added a solution of Dess-Martin reagent (3.05 g, 7.2 mmol) in 20 ml of dichloromethane. The mixture is stirred at room temperature for 2 hours. The reaction is quenched by the addition of saturated NaHCO$_3$ (50 ml) and Na$_2$S$_{2O3}$ (10.4 g, 42 mmol). The product is extracted with CH$_2$Cl$_2$ (50 ml) and dried over Na$_2$SO$_4$. The solvent is evaporated and the residue is purified by silica gel chromatography (Hexane:Acetone/1:1) to give the title compound.

Step 3d: Compound of Formula (I): W=—CH$_2$CH=CHCH$_2$—, X and Y taken together with the carbon atom they are attached to =C=N—OCH$_2$OCH$_3$, L=CH$_2$CH$_3$, Z=H and R$_x$=H;

A solution of the compound from step sc (440 mg, 0.6 mmol) in 5 ml ethanol is refluxed for 4 hours. The solvent is evaporated and the residue is dried in vacuo to give the title compound.

Example 4

Compound of Formula (I): W=—CH$_2$CH=CHCH$_2$—; X and Y taken together with the carbon atom they are attached to =C=O; L=CH$_2$CH$_3$; Z=H and R$_x$=H.

Step 4a: Compound: HO—CH$_2$—CH=CH—CH$_2$—O—Si(CH$_3$)(CH$_3$)(C(CH$_3$)$_3$);

A suspension of NaH (1.26 g, 50 mmol) in 40 ml of THF was added to a solution of diol (4.4 g, 50 mmol) in 30 ml of THF. The mixture was stirred at room temperature for 45 minutes and was added with a solution of tert-butyldimethylsilyl chloride (7.54 g, 50 mmol) in 30 ml of THF. The mixture was stirred at room temperature for 1 hour and quenched with saturated NaHCO$_3$ (200 ml) then extracted with ether (150 ml×2) and the combined organic layers were dried over MgSO$_4$. The solvent was removed and the resulting oil was purified on silica chromatography (Hexane:ethyl acetate/10:1) to give the title compound (8.4 g).

Step 4b: Compound: (CH$_3$)$_3$C—O—C(O)—O—CH$_2$—CH=CH—CH$_2$—O—Si(CH$_3$)(CH$_3$)(C(CH$_3$)$_3$);

A solution of compound from step 4a (8.1 g, 40 mmol) in 100 ml of methylenechloride was added to Boc$_2$O (13.1 g, 60 mmol), tetrabutylammoniumhydrogensulfate (1.2 g, 3.5 mmol) and 30 ml of 6N NaOH. The reaction mixture was stirred at room temperature for 16 hours, then diluted with 100 ml of methylene chloride and washed with saturated NaHCO$_3$ (200 ml×3). The organic layer was dried over Na$_2$SO$_4$. The solvent was removed and the residue was purified on silica gel chromatography (Hexane:ethylacetate/96:4) to give the title compound (6.8 g).

Step 4c: Compound of Formula (X): A=B=H, V taken together with the carbon atom it is attached to =C=NC(O)CH$_3$, R$_x$=R$_4$"=—C(O)CH$_3$ and R$^P_1$=—Si(CH$_3$)(CH$_3$)(C(CH$_3$)$_3$);

The compound from Step 4b—tert-Butyl-OC(O)—OCH$_2$CH=CHCH$_2$—O-tert-butyldimethylsilyl (0.9 g, 3 mmol), 1,4-bis(diphenylphosphino)butane (170 mg, 0.4 mmol) and Pd$_2$(dba)$_3$ (183 mg, 0.2 mmol) were added into a solution of ery-9-oxime triacetate (1.75 g, 2 mmol) in tetrahydrofuran (10 ml) at room temperature. The reaction mixture was refluxed under nitrogen overnight, cooled to room temperature and the solvent was removed in vacuo. The residue was purified by silica gel chromatography (acetone:hexanes/1:3) to give the title compound (1.5 g).

MS (ESI) m/z=1059.65 (M+H).

Step 4d: Compound of Formula (X): A=B=H, V taken together with the carbon atom it is attached to =C=N—OH, R$_x$=H, R$_4$"=C(O)CH$_3$ and R$^P_1$=—Si(CH$_3$)(CH$_3$)(C(CH$_3$)$_3$);

A solution of the compound from Step 4c (3.18 g, 3 mmol) in methanol (80 ml) was refluxed for 8 hours. The reaction was cooled to room temperature, the solvent was removed in vacuo and the residue was purified by silica gel chromatography (2M ammonia in methanol:dichloromethane/3:97) to give the title compound (2.6 g).

MS (ESI) m/z=975 (M+H).

Step 4e: Compound of Formula (X): A=B=H, V taken together with the carbon atom it is attached to =C=O, R$_x$=H, R$_4$"=C(O)CH$_3$ and R$^P_1$=H;

Formic acid (0.38 ml, 10 mmol) and Na$_2$S$_2$O$_4$ (1.39, 8 mmol) was added into an emulsion of the compound from Step 4d (2.44 g, 2.5 mmol) in isopropanol (25 ml) and water (30 ml). The mixture was heated to 90° C. and stirred at that temperature for 8 hours. The reaction mixture was cooled to room temperature, diluted with ethyl acetate (60 ml), washed with saturated sodium bicarbonate (3×60 ml), and dried over sodium sulfate. The solvent was removed in vacuo and the residue was purified by silica gel chromatography (2M ammonia in methanol:dichloromethane/3:97) to give the title compound (1.7 g).

MS (ESI) m/z=846 (M+H).

Step 4f: Compound of Formula (X): A=B=H, V taken together with the carbon atom it is attached to =C=O, R$_x$=C(O)CH$_3$, R$_4$"=C(O)CH$_3$ and R$^P_1$=H;

Acetic anhydride (94 μl, 1 mmol) was added into a solution of the compound from Step 4e (338.4mg, 0.4 mmol) in dichloromethane (5 ml). The mixture was stirred at room temperature for 16 hours. The solvent was removed in vacuo and the residue was purified by silica gel chromatography (acetone:hexane/4:6) to give the title compound (330 mg).

MS (ESI) m/z=888 (M+H).

Step 4g: Compound of Formula (X): A=B═H, V taken together with the carbon atom it is attached to ═C═O, $R_x$=C(O)CH$_3$, $R_4$"═C(O)CH$_3$ and $R^P_1$═C(O)—O—C(CH$_3$)$_3$;

Di-tert-butyl-dicarbonate (69 μl, 0.3 mmol) is added to a solution of the compound of Step 4f (178 mg, 0.2 mmol) and triethylamine (56 μl, 0.4 mmol) in dichloromethane (8 ml) at room temperature. After 10 minutes, N,N-dimethylamino pyridine (12.2 mg, 0.1 mmol) is added. The resulting solution is stirred at room temperature for 2 hours. The solvent is removed in vacuo and the residue is purified by silica gel chromatography (acetone:hexane/1:3) to give the title compound.

Step 4h: Compound of Formula (VIII): A=B═H, V taken together with the carbon atom it is attached to ═C═O and $R_4$"═C(O)CH$_3$;

1,4-Bis(diphenylphosphino)butane (8.5 mg, 0.02 mmol) and Pd$_2$(dba)$_3$ (9.2 mg, 0.01 mmol) is added to a solution of the compound of Step 4g (98.8 mg, 0.1 mmol) in 2 ml anhydrous THF at room temperature. The resulting mixture is refluxed for 30 minutes. The solvent is removed in vacuo and the residue is used for next step reaction without purification.

Step 4i: Compound of Formula (IX): A=B═H, V taken together with the carbon atom it is attached to ═C═O and $R_x$═C(O)CH$_3$;

To a solution of the compound of step 4h (700 mg, 0.8 mmol) in 10 ml of ethanol is added 1M HCl (25 ml). The mixture is heated to 75° C. and stirred at that temperature for 2 hours. The pH of the mixture is adjusted to pH=10 by addition of 2N NaOH and extracted with ethyl acetate (30 ml), then dried over Na$_2$SO$_4$ and the solvent is evaporated. The residue is purified on silica gel chromatography (acetone:hexane/1:3) to give the title compound.

Step 4j: Compound of Formula (I): W═—CH$_2$—CH═CHCH$_2$—, X and Y taken together with the carbon atom they are attached to ═C═O, L=CH$_2$CH$_3$, Z=H and $R_x$═C(O)CH$_3$;

To a solution of compound of Step 4i (480 mg, 0.7 mmol) in 10 ml CH$_2$Cl$_2$ is added Dess-Martin reagent (385 mg, 0.9 mmol) at room temperature. The reaction mixture is stirred at room temperature for 2 hours, then quenched with NaHCO$_3$ and Na$_2$S$_2$O$_3$ (0.4g). The organic layer is separated and dried over Na$_2$SO$_4$. The solvent is evaporated and the residue is purified on silica gel chromatography (acetone:hexane/1:3) to give the title compound.

Step 4k: Compound of Formula (I): W═—CH$_2$CH═CHCH$_2$—, X and Y taken together with the carbon atom they are attached to ═C═O, L=CH$_2$CH$_3$, Z=H and $R_x$=H;

A solution of the compound of Step 4j (300 mg, 0.45 mmol) in 10 ml methanol is refluxed for 18 hours. The solvent is evaporated and the residue is purified on silica gel chromatography (CH$_2$Cl$_2$: 2M ammonia in methanol/95:5) to give the title compound.

Example 5

Compound of Formula (V): Q═—C(C$_6$H$_5$)═N—O—; X and Y taken together with the carbon atom they are attached to ═C═NC(O)CH$_3$; Z=H and $R_x$=H.

Step 5a: Compound of Formula (VIII): A=B═H, V taken together with the carbon atom it is attached to ═C═NH, $R_4$"═C(O)C$_6$H$_5$ and $R_x$=H;

The compound from step 1c in methanol is treated with titanium trichloride (20% in 3% hydrochloric acid) following the procedure described in step 1d except the reaction is quenched with aqueous sodium bicarbonate after 2–3 hours. The aqueous solution is extracted with methylene chloride 4 times and the organic phase is combined and dried over sodium sulfate. The solvent is then removed under vacuum and the crude residue is purified by chromatography on a silica gel column to provide the title compound.

Step 5b: Compound of Formula (VIII): A=B═H, V taken together with the carbon atom it is attached to ═C═NC(O)CH$_3$, $R_4$"═C(O)C$_6$H$_5$ and $R_x$═C(O)CH$_3$;

The compound from step 5a is treated with 2.5 equivalents acetic anhydride and triethylamine in dichloromethane. The reaction mixture is stirred at room temperature for 3 hours, then diluted with dichloromethane and washed with saturated sodium bicarbonate and brine. The organic phase is dried over sodium sulfate and the solvent is removed in vacuo. The residue is purified by silica gel chromatography (hexanes:acetone/1:1) to give the title compound.

Step 5c: Compound of Formula (XI): Q═—C(C$_6$H$_5$)═N—O—, V taken together with the carbon atom it is attached to ═C═NC(O)CH$_3$, $R_4$"═C(O)C$_6$H$_5$ and $R_x$═C(O)CH$_3$;

To a solution of benzaldoxime (1.2 mmol) in 5 mL ethyl acetate is added NCS (0.17g, 1.2 mmol) and NaHCO$_3$ (0.25g, 2.5 mmol) and 1 drop of water. The compound from step 5b (1.0 mmol) is added to the reaction mixture and stirred at room temperature for 12 hours. Then the reaction mixture is diluted with ethyl acetate, washed with saturated aqueous NaHCO$_3$, and dried over anhydrous Na$_2$SO$_4$. The solvent is evaporated and the residue purified on silica gel column gives the title compound.

Step 5d: Compound of Formula (XII): Q═—C(C$_6$H$_5$)═N—O—, V taken together with the carbon atom it is attached to ═C═NC(O)CH$_3$, and $R_x$═C(O)CH$_3$;

The compound from step 5c (0.5 mmol) in ethanol (5 mL) and 0.5 N HCl (4 mL) is heated at 60° C. for 2 hours. Then 20 ml of saturated aqueous NaHCO$_3$ is added and the aqueous layer is extracted 3 times with CH$_2$Cl$_2$. The combined organic layer is dried over anhydrous Na$_2$SO$_4$. The solvent is concentrated under vacuum and the residue is purified on a silica gel column to provide the title compound.

Step 5e: Compound of Formula (V): Q═—C(C$_6$H$_5$)═N—O—, X and Y taken together with the carbon atom they are attached to ═C═NC(O)CH$_3$, Z=H and $R_x$=H;

The compound from step 5d is converted to the title compound following the procedures described in step 1f and 1g.

Example 6

Compound of Formula (V): Q=—O—C(O)—O—; X and Y taken together with the carbon atom they are attached to =C=NC(O)CH$_3$; Z=H and R$_x$=H.

Step 6a: Compound of Formula (XVII): E=G=—OH, V taken together with the carbon atom it is attached to =C=NC(O)CH$_3$, R$_x$=C(O)CH$_3$ and R$_4$"=C(O)C$_6$H$_5$;

To a solution of the compound from step 5b (1.0 mmol) and NMO (1.2 mmol) in 5 mL t-butanol is added 4% OsO$_4$ (catalytic amount). The reaction mixture is stirred for 3 hours at room temperature. The solvent is then removed under vacuum and the crude residue is purified by chromatography on a silica gel column to provide the title compound.

Step 6b: Compound of Formula (XI): Q=—O—C(O)—O—, V taken together with the carbon atom it is attached to =C=NC(O)CH$_3$, R$_4$"=C(O)C$_6$H$_5$ and R$_x$=C(O)CH$_3$;

The compound from step 6a (1.0 mmol), CDI (1.2 mmol) and 0.2 mL triethylamine are dissolved in 15 mL methylene chloride. The reaction mixture is stirred for 12 hours at room temperature. The reaction is quenched with NaHCO$_3$ aqueous solution and extracted with methylene chloride. The combined organic layers are dried over anhydrous Na$_2$SO$_4$. The solvent is evaporated and the residue is purified by chromatography on a silica gel column to provide the title compound.

Step 6c: Compound of Formula (V): Q=—O—C(O)—O—, X and Y taken together with the carbon atom they are attached to =C=NC(O)CH$_3$, Z=H and R$_x$=H;

The compound from step 6b is converted to the title compound following the procedures described in step 5d and 5e.

Example 7

Compound of Formula (V): Q=—O—; X and Y taken together with the carbon atom they are attached to =C=NC(O)CH$_3$; Z=H and R$_x$=H.

Step 7a: Compound of Formula (XI): Q=—O—, V taken together with the carbon atom it is attached to =C=NC(O)CH$_3$, R$_4$"=C(O)C$_6$H$_5$, and R$_x$=C(O)CH$_3$, To a solution of the compound from step 5b (1.0 mmol) in CH$_2$Cl$_2$ is added m-CPBA (1.2 mmol). The reaction mixture is stirred for 3 hours at room temperature. The solvent is then removed under vacuum and the crude residue is purified by chromatography on a silica gel column to provide the title compound.

Step 7b: Compound of Formula (V): Q=—O—, X and Y taken together with the carbon atom they are attached to =C=NC(O)CH$_3$, Z=H and R$_x$=H;

The compound from step 7a is converted to the title compound following the procedures described in step 5d and 5e.

Example 8

Compound of Formula (I): W=—CH$_2$—CH=CH—CH$_2$—; X and Y taken together with the carbon atom they are attached to =C=NC(O)CH$_2$OCH$_3$; L=CH$_2$CH$_3$; Z=H and R$_x$=H.

Step 8a: Compound of Formula (VIII): A=B=H, V taken together with the carbon atom it is attached to =C=NC(O)CH$_2$OCH$_3$, R$_4$"=C(O)C$_6$H$_5$ and R$_x$=C(O)CH$_2$OCH$_3$;

To a solution of methoxyacetic acid (2.5 mmol) in CH$_2$C$_{12}$ is added DCC (2.5 mmol) at 0° C. The mixture is stirred for 10 minutes. The compound from step 5a (1.0 mmol) in CH2Cl2 is added and the solution is stirred for 12 hours. The solvent is removed under vacuum and the residue is purified on a silica gel column to provide the title compound.

Step 8b: Compound of Formula (I): W=—CH$_2$—CH=CH—CH$_2$—, X and Y taken together with the carbon atom they are attached to =C=NC(O) CH$_2$OCH$_3$, L=CH$_2$CH$_3$, Z=H and R$_x$=H;

The compound from step 8a is converted to the title compound following the procedures described in step 5d and 5e.

Example 9

Compound of Formula (III a): A=3-quinolyl; B=H, X and Y taken together with the carbon atom they are attached to =C=NC(O)CH$_3$; Z=H and R$_x$=H;

Step 9a: Compound of Formula (XIII): A=3-quinolyl, B=H, V taken together with the carbon atom it is attached to =C=NC(O)CH$_3$, R$_4$"=C(O)C$_6$H$_5$ and R$_x$=C(O)CH$_3$;

The compound from step 5b (0.50 mmol), 3-bromoquinoline (0.21 g, 1.0 mmol), Pd(OAc)$_2$ (15 mg, 0.07 mmol), (o-Tolyl)$_3$P (50 mg, 0.16 mmol) and triethyl amine (0.5 mL, 4.0 mmol) are dissolved in 10 mL CH$_3$CN and the solution is degassed at −40° C. The reaction mixture is warmed up to room temperature and sealed under nitrogen, then is heated at 50° C. for 1.5 hours, then left at 78° C. for 12 hours. Then the reaction mixture is diluted with ethyl acetate, washed with saturated aqueous NaHCO$_3$, and dried over anhydrous Na$_2$SO$_4$. The solvent is evaporated and the residue is purified by chromatography on a silica gel column to provide the title compound.

Step 9b: Compound of Formula (III a): A=3-quinolyl, B=H, X and Y taken together with the carbon atom they are attached to =C=NC(O)CH$_3$, Z=H and R$_x$=H;

The compound from step 9a is converted to the title compound following the procedures described in step 5d and 5e.

Example 10

Compound of Formula (I): W=—CH$_2$—C(CH=CH—C$_6$H$_5$)=CH—CH$_2$—; X and Y taken together with the carbon atom they are attached to =C=NC(O)CH$_3$; L=CH$_2$CH$_3$; Z=H and R$_x$=H;

Step 10a: Compound of Formula (VIII): A=—CH=CH—C$_6$H$_5$, B=H, V taken together with the carbon atom it is attached to =C=NC(O)CH$_3$, R$_4$"=C(O)C$_6$H$_5$ and R$_x$=C (O)CH$_3$;

Compound from step 5b (1.0 equiv.) is dissolved in anhydrous DMF. β-bromostyrene (3.0 equiv.) and K$_2$CO$_3$ (4 equiv.) are added at room temperature. The mixture is degassed briefly and a catalytic amount of dihydrogen dichlorobis(di-tert-butylphosphinito-kP)palladate(2-) (POPd from Combiphos catalysts, Inc.) is added. The reaction mixture is heated to 100° C. in a sealed tube for 48 hours. Ethyl acetate is added and the solution is washed 3 times with NaHCO$_3$ aqueous solution. The organic layer is dried over anhydrous Na$_2$SO$_4$. The solvent is evaporated under vacuum and the residue is purified by chromatography on a silica gel column to provide the title compound.

Step 10b: Compound of Formula (I): W=—CH$_2$—C(CH=CH—C$_6$H$_5$)=CH—CH$_2$—, X and Y taken together with the carbon atom they are attached to =C=NC(O)CH$_3$, L=CH$_2$CH$_3$, Z=H and R$_x$=H;

The compound from step 9a is converted to the title compound following the procedures described in step 5d and 5e.

Although the invention has been described in detail with respect to various preferred embodiments it is not intended to be limited thereto, but rather those skilled in the art will recognize that variations and modifications may be made therein which are within the spirit of the invention and the scope of the appended claims.

What is claimed is:

1. A process for preparing a compound of formula:

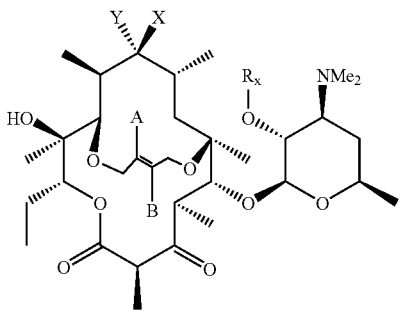

comprising the steps of:

a) removing the cladinose moiety, by hydrolysis with an acid, from a compound of formula:

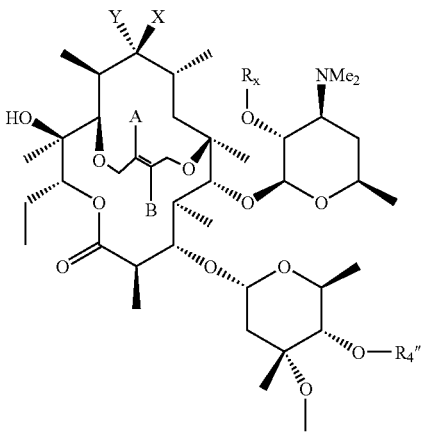

wherein:
R$_4$ is a hydroxy protecting group or H,
A and B are independently selected from the group consisting of:
 (i) hydrogen;
 (ii) deuterium;
 (iii) halogen;
 (iv) R$_1$, wherein R$_1$ is selected from the group consisting of:
  a. C$_1$–C$_6$ alkyl, optionally substituted with one or more substituents selected from the group consisting of: halogen, aryl, substituted aryl, heteroaryl, and substituted heteroaryl;
  b. C$_2$–C$_6$ alkenyl, optionally substituted with one or more substituents selected from the group consisting of: halogen, aryl, substituted aryl, heteroaryl, and substituted heteroaryl; and
  c. C$_2$–C$_6$ alkynyl, optionally substituted with one or more substituents selected from the group consisting of: halogen, aryl, substituted aryl, heteroaryl, and substituted heteroaryl;
 (v) R$_2$, wherein R$_2$ is selected from the group consisting of:
  a. aryl;
  b. heteroaryl;
  c. substituted aryl; and
  d. substituted heteroaryl;
 (vi) —(C$_1$–C$_3$-alkyl)-M-(C$_1$–C$_3$-alkyl)-R$_2$, wherein M=—O—, —NH—, —N(CH$_3$)—, —NHC(O)— or —S(O)$_n$—, wherein n=0, 1 or 2, and R$_2$ is as previously defined;
 (vii) —(C$_1$–C$_3$-alkyl)-M-R$_2$, wherein M and R$_2$ are as previously defined;
 (viii) —C(O)-J-R$_3$, wherein J is absent, O or S, and R$_3$ is H, R$_1$ or R$_2$; where R$_1$ and R$_2$ are as previously defined, and
 (ix) —C(O)—NR$_{11}$R$_{12}$, wherein R$_{11}$ and R$_{12}$ are each independently selected from the group consisting of:
  a. hydrogen;
  b. C$_1$–C$_6$-alkyl, optionally substituted with one or more substituents selected from the group consisting of: halogen, aryl, substituted aryl, heteroaryl, and substituted heteroaryl;
  c. C$_2$–C$_6$-alkenyl, optionally substituted with one or more substituents selected from the group consisting of: halogen, aryl, substituted aryl, heteroaryl, and substituted heteroaryl;
  d. C$_2$–C$_6$-alkynyl, optionally substituted with one or more substituents selected from the group consisting of: halogen, aryl, substituted aryl, heteroaryl, and substituted heteroaryl; and
  e. R$_{11}$ and R$_{12}$ taken together with the nitrogen atom to which they are connected form a 3- to 7-membered ring which may optionally contain one or more heterofunctions selected from the group consisting of: —O—, —NH—, —N(C$_1$–C$_6$-alkyl)-, —N(R$_2$)—, —S(O)$_n$—, wherein n and R$_2$ are as previously defined;

X and Y are:
 (a) independently selected from the group consisting of:
  (i) hydrogen;
  (ii) deuterium;
  (iii) —OH;
  (iv) —OR$^p$, wherein R$^p$ is a hydroxy protecting group; and
  (v) —NR$_{14}$R$_{15}$, wherein R$_{14}$ and R$_{15}$ are each independently selected from the group consisting of:
   a. hydrogen;
   b. C$_1$–C$_{12}$ alkyl, optionally substituted with one or more substituents selected from the group consisting of halogen, aryl, substituted aryl, heteroaryl and substituted heteroaryl; and
   c. R$_{14}$ and R$_{15}$, taken together with the nitrogen atom to which they are attached form a 3 to 10 membered heterocycloalkyl ring optionally substituted with one or more hetero atoms selected from the group consisting of O, S and N; or (b) taken together with the carbon atom to which they are attached are selected from the group consisting of:
  (i) C═O;
  (ii) C═NR$_3$, wherein R$_3$ is as previously defined;
  (iii) C═NC(O)R$_3$, wherein R$_3$ is as previously defined;
  (iv) C═N—OR$_6$, wherein R$_6$ is selected from the group consisting of:
    a. hydrogen;
    b. —CH$_2$O(CH$_2$)$_2$OCH$_3$;
    c. —CH$_2$O(CH$_2$O)$_n$CH$_3$, wherein n is as previously defined;
    d. C$_1$–C$_{12}$ alkyl, optionally substituted with one or more substituents selected from the group consisting of halogen, aryl, substituted aryl, heteroaryl and substituted heteroaryl;
    e. C$_3$–C$_{12}$ cycloalkyl;
    f. C(O)—C$_1$–C$_{12}$ alkyl;
    g. C(O)—C$_3$–C$_{12}$ cycloalkyl;
    h. C(O)—R$_2$, wherein R$_2$ is as previously defined; and
    i. —Si(R$_a$)(R$_b$)(R$_c$), wherein R$_a$, R$_b$ and R$_c$ are each independently selected from the group consisting of C$_1$–C$_{12}$ alkyl, aryl and substituted aryl;
  (v) C═N—O—C(R$_{16}$)(R$_{17}$)—O—R$_{18}$, wherein R$_{16}$ and R$_{17}$ taken together with the carbon atom to which they are attached form a C$_3$ to C$_{12}$ cycloalkyl group or each independently is selected from the group consisting of: hydrogen, and C$_1$–C$_{12}$ alkyl; and R$_{18}$ is selected from the group consisting of:
    a. hydrogen;
    b. —CH$_2$O(CH$_2$)$_2$OCH$_3$;
    c. —CH$_2$O(CH$_2$O)$_n$CH$_3$, wherein n is as previously defined;
    d. C$_1$–C$_{12}$ alkyl, optionally substituted with one or more substituents selected from the group consisting of halogen, aryl, substituted aryl, heteroaryl and substituted heteroaryl;
    e. C$_3$–C$_{12}$ cycloalkyl; and
    f. —Si(R$_a$)(R$_b$)(R$_c$), wherein R$_a$, R$_b$ and R$_c$ are as previously defined;
R$_x$ is hydrogen or R$^p$, wherein R$^p$ is as previously defined;
b) oxidizing the compound from step (a) with an oxidizing agent; and
c) optionally deprotecting the 2' hydroxy group.

2. A process for preparing a compound of formula:

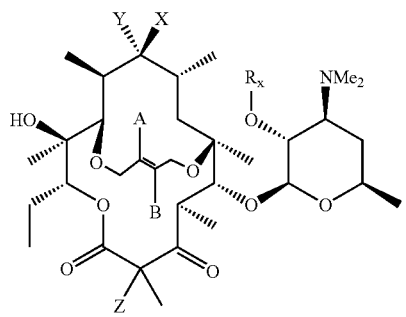

wherein Z is a halogen;
comprising the step of reacting a compound of formula:

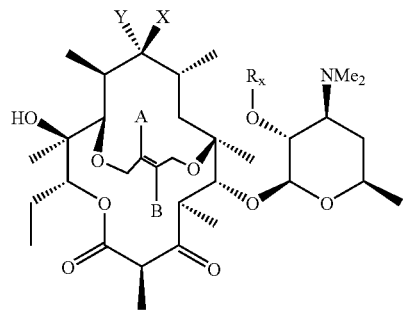

wherein A, B, X, Y, and R$_x$ are as defined in claim 1, with a halogenating agent in the presence of an acid or base.

3. The process of claim 2 further comprising the step of deprotecting the hydroxy protecting group when R$_x$ is a hydroxy protecting group.

4. A process for preparing a compound of formula;

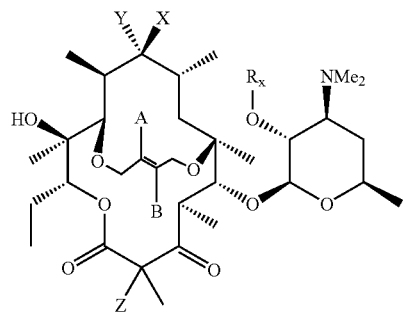

wherein Z is a methyl group:
comprising the step of reacting a compound of formula:

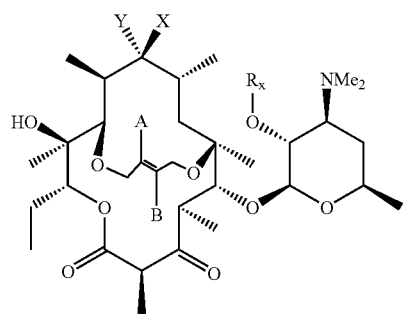

wherein A, B, X, Y, and R$_x$ are as defined in claim 1, with methyl iodide in the presence of a base, optionally using a phase transfer catalyst.

5. The process of claim 4 further comprising the step of deprotecting the hydroxy protecting group when R$_x$ is a hydroxy protecting group.

* * * * *